(12) United States Patent
Lau et al.

(10) Patent No.: US 8,447,822 B2
(45) Date of Patent: *May 21, 2013

(54) METHOD AND SYSTEM FOR ENHANCED MESSAGING

(75) Inventors: Chung Lau, Sunnyvale, CA (US); C. Douglass Thomas, Saratoga, CA (US)

(73) Assignee: IpVenture, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,025

(22) Filed: Apr. 27, 2012

(65) Prior Publication Data
US 2012/0220266 A1    Aug. 30, 2012

Related U.S. Application Data

(63) Continuation of application No. 13/113,972, filed on May 23, 2011, now Pat. No. 8,176,135, which is a continuation of application No. 12/214,434, filed on Jun. 19, 2008, now Pat. No. 7,953,809, which is a continuation of application No. 10/397,474, filed on Mar. 26, 2003, now Pat. No. 7,403,972.

(60) Provisional application No. 60/444,198, filed on Jan. 30, 2003, provisional application No. 60/418,491, filed on Oct. 15, 2002, provisional application No. 60/404,645, filed on Aug. 19, 2002, provisional application No. 60/375,998, filed on Apr. 24, 2002.

(51) Int. Cl.
*G06F 15/16* (2006.01)
*G06F 12/00* (2006.01)

(52) U.S. Cl.
USPC .......................................... 709/206; 709/207

(58) Field of Classification Search
USPC ................. 709/206–207, 217–218, 225–229, 709/250
See application file for complete search history.

(56) References Cited

U.S. PATENT DOCUMENTS

| | | | |
|---|---|---|---|
| 5,337,579 A | 8/1994 | Saia, III et al. | |
| 5,347,274 A | 9/1994 | Hassett | |
| 5,389,934 A | 2/1995 | Kass | |
| 5,400,020 A | 3/1995 | Jones et al. | |
| 5,461,365 A | 10/1995 | Schlager et al. | |
| 5,491,486 A | 2/1996 | Welles, II et al. | |

(Continued)

FOREIGN PATENT DOCUMENTS

| | | |
|---|---|---|
| EP | 0 874 529 A2 | 10/1998 |
| EP | 1 037 447 A2 | 9/2000 |

(Continued)

OTHER PUBLICATIONS

Office Action for U.S. Appl. No. 10/397,474, dated Aug. 23, 2006.

(Continued)

*Primary Examiner* — Zarni Maung

(57) ABSTRACT

Techniques for acquiring, sending, receiving or using status information from a remote location over a network are disclosed. The status information is transmitted over the network between or among electronic devices. The status information can be provided by one or more sensors associated with the electronic device that is transmitting the status information. The status information can be transmitted with messages so as to enhance the messages. The electronic devices include at least computing devices, such as personal computers, personal digital assistants, pagers, and mobile telephones.

40 Claims, 7 Drawing Sheets

U.S. PATENT DOCUMENTS

| | | | |
|---|---|---|---|
| 5,512,902 A | 4/1996 | Guthrie et al. |
| 5,515,858 A | 5/1996 | Myllymaki |
| 5,528,247 A | 6/1996 | Nonami |
| 5,528,518 A | 6/1996 | Bradshaw et al. |
| 5,532,690 A | 7/1996 | Hertel |
| 5,539,748 A | 7/1996 | Raith |
| 5,541,845 A | 7/1996 | Klein |
| 5,550,551 A | 8/1996 | Alesio |
| 5,568,119 A | 10/1996 | Schipper et al. |
| 5,570,412 A | 10/1996 | LeBlanc |
| 5,576,716 A | 11/1996 | Sadler |
| 5,592,173 A | 1/1997 | Lau et al. |
| 5,598,460 A | 1/1997 | Tendler |
| 5,604,708 A | 2/1997 | Helms et al. |
| 5,623,260 A | 4/1997 | Jones |
| 5,623,418 A | 4/1997 | Rostoker |
| 5,629,678 A | 5/1997 | Gargano et al. |
| 5,633,874 A | 5/1997 | Diachina et al. |
| 5,650,770 A | 7/1997 | Schlager et al. |
| 5,652,570 A | 7/1997 | Lepkofker |
| 5,673,692 A | 10/1997 | Schulze et al. |
| 5,686,888 A | 11/1997 | Welles, II et al. |
| 5,710,551 A | 1/1998 | Ridgeway |
| 5,712,619 A | 1/1998 | Simkin |
| 5,731,757 A | 3/1998 | Layson et al. |
| 5,731,788 A | 3/1998 | Reeds |
| 5,742,233 A | 4/1998 | Hoffman et al. |
| 5,751,245 A | 5/1998 | Janky et al. |
| 5,771,001 A | 6/1998 | Cobb |
| 5,771,455 A | 6/1998 | Kennedy, III et al. |
| 5,774,876 A | 6/1998 | Woolley et al. |
| 5,797,091 A | 8/1998 | Clise et al. |
| 5,808,565 A | 9/1998 | Matta et al. |
| RE35,920 E | 10/1998 | Sorden et al. |
| 5,825,283 A | 10/1998 | Camhi |
| 5,826,195 A | 10/1998 | Westerlage et al. |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,861,841 A | 1/1999 | Gildea et al. |
| 5,883,594 A | 3/1999 | Lau |
| 5,889,770 A | 3/1999 | Jokiaho et al. |
| 5,892,454 A | 4/1999 | Schipper et al. |
| 5,905,461 A | 5/1999 | Neher |
| 5,910,799 A | 6/1999 | Carpenter et al. |
| 5,913,078 A | 6/1999 | Kimura et al. |
| 5,917,433 A | 6/1999 | Keillor et al. |
| 5,918,180 A | 6/1999 | Dimino |
| 5,938,721 A | 8/1999 | Dussell et al. |
| 5,948,040 A | 9/1999 | DeLorme et al. |
| 5,948,043 A | 9/1999 | Mathis |
| 5,959,575 A | 9/1999 | Abbott |
| 5,959,577 A | 9/1999 | Fan et al. |
| 5,963,130 A | 10/1999 | Schlager et al. |
| 5,982,285 A | 11/1999 | Bueche et al. |
| 5,982,807 A | 11/1999 | Snell |
| 5,983,108 A | 11/1999 | Kennedy, III et al. |
| 5,991,690 A | 11/1999 | Murphy |
| 5,995,849 A | 11/1999 | Williams et al. |
| 6,002,363 A | 12/1999 | Krasner |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,023,241 A | 2/2000 | Clapper |
| 6,031,496 A | 2/2000 | Kuittinen |
| 6,032,051 A | 2/2000 | Hall et al. |
| 6,034,622 A | 3/2000 | Levine |
| 6,054,928 A | 4/2000 | Lemelson |
| 6,064,336 A | 5/2000 | Krasner |
| 6,067,018 A | 5/2000 | Skelton et al. |
| 6,067,044 A | 5/2000 | Whelan et al. |
| 6,072,396 A | 6/2000 | Gaukel |
| 6,078,290 A | 6/2000 | McBurney et al. |
| 6,083,248 A | 7/2000 | Thompson |
| 6,083,353 A | 7/2000 | Alexander |
| 6,094,168 A | 7/2000 | Duffett-Smith et al. |
| 6,100,806 A | 8/2000 | Gaukel |
| 6,101,710 A | 8/2000 | Selinger |
| 6,111,540 A | 8/2000 | Krasner |
| 6,115,595 A | 9/2000 | Rodal et al. |
| 6,121,921 A | 9/2000 | Ishigaki |
| 6,131,067 A | 10/2000 | Girerd et al. |
| 6,140,863 A | 10/2000 | Fujisawa |
| 6,141,570 A | 10/2000 | O'Neill, Jr. et al. |
| 6,144,303 A | 11/2000 | Federman |
| 6,148,280 A | 11/2000 | Kramer |
| 6,154,422 A | 11/2000 | Shinkawa et al. |
| 6,163,696 A | 12/2000 | Bi et al. |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,212,133 B1 | 4/2001 | McCoy et al. |
| 6,226,622 B1 | 5/2001 | Dabbiere |
| 6,231,519 B1 | 5/2001 | Blants et al. |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,252,543 B1 | 6/2001 | Camp |
| 6,263,280 B1 | 7/2001 | Stingone, Jr. |
| 6,278,936 B1 | 8/2001 | Jones |
| 6,281,797 B1 | 8/2001 | Forster |
| 6,282,362 B1 | 8/2001 | Murphy et al. |
| 6,282,495 B1 | 8/2001 | Kirkhart et al. |
| 6,292,687 B1 | 9/2001 | Lowell et al. |
| 6,298,306 B1 | 10/2001 | Suarez et al. |
| 6,300,875 B1 | 10/2001 | Schafer |
| 6,302,844 B1 | 10/2001 | Walker et al. |
| 6,304,467 B1 | 10/2001 | Nebrigic |
| 6,314,308 B1 | 11/2001 | Sheynblat et al. |
| 6,317,049 B1 | 11/2001 | Toubia et al. |
| 6,323,807 B1 | 11/2001 | Golding et al. |
| 6,324,213 B1 | 11/2001 | Harrison |
| 6,327,533 B1 | 12/2001 | Chou |
| 6,331,817 B1 | 12/2001 | Goldberg |
| 6,339,397 B1 | 1/2002 | Baker |
| 6,340,928 B1 | 1/2002 | McCurdy |
| 6,342,847 B1 | 1/2002 | Archuleta et al. |
| 6,349,257 B1 | 2/2002 | Liu et al. |
| 6,353,390 B1 | 3/2002 | Beri et al. |
| 6,353,798 B1 | 3/2002 | Green et al. |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,373,430 B1 | 4/2002 | Beason et al. |
| 6,377,810 B1 | 4/2002 | Geiger et al. |
| 6,388,612 B1 | 5/2002 | Neher |
| 6,393,346 B1 | 5/2002 | Keith et al. |
| 6,404,352 B1 | 6/2002 | Ichikawa et al. |
| 6,407,698 B1 | 6/2002 | Ayed |
| 6,411,892 B1 | 6/2002 | Van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,430,602 B1 | 8/2002 | Kay et al. |
| 6,433,732 B1 | 8/2002 | Dutta et al. |
| 6,434,396 B1 | 8/2002 | Rune |
| 6,441,778 B1 | 8/2002 | Durst et al. |
| 6,442,380 B1 | 8/2002 | Mohindra |
| 6,442,391 B1 | 8/2002 | Johansson et al. |
| 6,443,890 B1 | 9/2002 | Schulze et al. |
| 6,445,937 B1 | 9/2002 | daSilva |
| 6,453,237 B1 | 9/2002 | Fuchs et al. |
| 6,463,272 B1 | 10/2002 | Wallace et al. |
| 6,466,821 B1 | 10/2002 | Pianca et al. |
| 6,469,639 B2 | 10/2002 | Tanenhaus et al. |

| | | |
|---|---|---|
| 6,471,087 B1 | 10/2002 | Shusterman |
| 6,478,736 B1 | 11/2002 | Mault |
| 6,496,775 B2 | 12/2002 | McDonald, Jr. et al. |
| 6,505,048 B1 | 1/2003 | Moles et al. |
| 6,505,049 B1 | 1/2003 | Dorenbosch |
| 6,513,532 B2 | 2/2003 | Mault et al. |
| 6,522,871 B1 | 2/2003 | Patrick et al. |
| 6,522,889 B1 | 2/2003 | Aarnio |
| 6,529,164 B1 | 3/2003 | Carter |
| 6,544,193 B2 | 4/2003 | Abreu |
| 6,552,652 B2 | 4/2003 | Beken |
| 6,553,336 B1 | 4/2003 | Johnson et al. |
| 6,559,620 B2 | 5/2003 | Zhou et al. |
| 6,569,094 B2 | 5/2003 | Suzuki et al. |
| 6,579,231 B1 | 6/2003 | Phipps |
| 6,579,844 B1 | 6/2003 | Morrison et al. |
| 6,611,688 B1 | 8/2003 | Raith |
| 6,625,437 B1 | 9/2003 | Jampolsky et al. |
| 6,630,885 B2 | 10/2003 | Hardman et al. |
| 6,640,085 B1 | 10/2003 | Chatzipetros et al. |
| 6,650,907 B1 | 11/2003 | Kamperschroer et al. |
| 6,661,372 B1 | 12/2003 | Girerd et al. |
| 6,679,071 B1 | 1/2004 | Storey et al. |
| 6,696,982 B2 | 2/2004 | Yoshioka et al. |
| 6,714,791 B2 | 3/2004 | Friedman |
| 6,721,542 B1 | 4/2004 | Anttila et al. |
| 6,741,927 B2 | 5/2004 | Jones |
| 6,747,675 B1 | 6/2004 | Abbott et al. |
| 6,748,318 B1 | 6/2004 | Jones |
| 6,788,766 B2 | 9/2004 | Logan |
| 6,801,853 B2 | 10/2004 | Workman |
| 6,804,606 B2 | 10/2004 | Jones |
| 6,847,892 B2 | 1/2005 | Zhou et al. |
| 6,856,804 B1 | 2/2005 | Ciotta |
| 6,865,385 B1 | 3/2005 | Kohda et al. |
| 6,937,900 B1 | 8/2005 | Pianca et al. |
| 6,952,645 B1 | 10/2005 | Jones |
| 6,975,941 B1 | 12/2005 | Lau et al. |
| 6,980,826 B2 | 12/2005 | Yamaguchi |
| 7,010,144 B1 | 3/2006 | Davis et al. |
| 7,071,842 B1 | 7/2006 | Brady, Jr. |
| 7,085,253 B2 | 8/2006 | Yang |
| 7,110,773 B1 | 9/2006 | Wallace et al. |
| 7,136,832 B2 | 11/2006 | Li et al. |
| 7,187,278 B2 | 3/2007 | Biffar |
| 7,212,829 B1 | 5/2007 | Lau et al. |
| 7,218,938 B1 | 5/2007 | Lau et al. |
| 7,253,731 B2 | 8/2007 | Joao |
| 7,321,774 B1 | 1/2008 | Lau et al. |
| 7,325,061 B2 | 1/2008 | Haruki |
| 7,366,522 B2 | 4/2008 | Thomas |
| 7,403,972 B1 | 7/2008 | Lau et al. |
| 7,539,557 B2 | 5/2009 | Yamauchi |
| 7,809,377 B1 | 10/2010 | Lau et al. |
| 7,905,832 B1 | 3/2011 | Lau et al. |
| 7,953,809 B2 * | 5/2011 | Lau et al. .................. 709/206 |
| 8,176,135 B2 * | 5/2012 | Lau et al. .................. 709/206 |
| 8,285,484 B1 | 10/2012 | Lau et al. |
| 8,301,158 B1 | 10/2012 | Thomas |
| 2001/0006891 A1 | 7/2001 | Cho |
| 2001/0020204 A1 | 9/2001 | Runyon et al. |
| 2001/0027378 A1 | 10/2001 | Tennison et al. |
| 2001/0027525 A1 | 10/2001 | Gamlin |
| 2001/0028304 A1 | 10/2001 | I'Anson et al. |
| 2001/0044299 A1 | 11/2001 | Sandegren |
| 2001/0044332 A1 | 11/2001 | Yamada et al. |
| 2001/0052849 A1 | 12/2001 | Jones, Jr. |
| 2002/0000930 A1 | 1/2002 | Crowson et al. |
| 2002/0016173 A1 | 2/2002 | Hunzinger |
| 2002/0027507 A1 | 3/2002 | Yarin et al. |
| 2002/0036593 A1 | 3/2002 | Ying |
| 2002/0038182 A1 | 3/2002 | Wong et al. |
| 2002/0049742 A1 | 4/2002 | Chan et al. |
| 2002/0050945 A1 | 5/2002 | Tsukishima et al. |
| 2002/0057192 A1 | 5/2002 | Eagleson et al. |
| 2002/0063622 A1 | 5/2002 | Armstrong et al. |
| 2002/0071677 A1 | 6/2002 | Sumanaweera |
| 2002/0077080 A1 | 6/2002 | Greene |
| 2002/0087260 A1 | 7/2002 | Hancock et al. |
| 2002/0087619 A1 | 7/2002 | Tripathi |
| 2002/0094067 A1 | 7/2002 | August |
| 2002/0111171 A1 | 8/2002 | Boesch et al. |
| 2002/0111819 A1 | 8/2002 | Li et al. |
| 2002/0115453 A1 | 8/2002 | Poulin et al. |
| 2002/0119770 A1 | 8/2002 | Twitchell et al. |
| 2002/0119789 A1 | 8/2002 | Friedman |
| 2002/0120475 A1 | 8/2002 | Morimoto |
| 2002/0120503 A1 | 8/2002 | Iwayama et al. |
| 2002/0140081 A1 | 10/2002 | Chou et al. |
| 2002/0173910 A1 | 11/2002 | McCall et al. |
| 2002/0193121 A1 | 12/2002 | Nowak et al. |
| 2003/0003943 A1 | 1/2003 | Bajikar |
| 2003/0009410 A1 | 1/2003 | Ramankutty et al. |
| 2003/0013445 A1 | 1/2003 | Fujiwara et al. |
| 2003/0069759 A1 | 4/2003 | Smith |
| 2003/0083011 A1 | 5/2003 | Haller et al. |
| 2003/0095540 A1 | 5/2003 | Mulligan et al. |
| 2003/0151507 A1 | 8/2003 | Andre et al. |
| 2003/0163287 A1 | 8/2003 | Vock |
| 2003/0204132 A1 | 10/2003 | Suzuki et al. |
| 2004/0034470 A1 | 2/2004 | Workman |
| 2004/0046637 A1 | 3/2004 | Wesby Van Swaay |
| 2004/0114731 A1 | 6/2004 | Gillett et al. |
| 2004/0117108 A1 | 6/2004 | Nemeth |
| 2004/0233065 A1 | 11/2004 | Freeman |
| 2006/0173444 A1 | 8/2006 | Choy et al. |
| 2007/0156286 A1 | 7/2007 | Yamauchi |
| 2008/0021645 A1 | 1/2008 | Lau et al. |
| 2008/0261636 A1 | 10/2008 | Lau et al. |
| 2009/0042540 A1 | 2/2009 | Bodnar et al. |
| 2011/0022533 A1 | 1/2011 | Lau et al. |
| 2011/0223884 A1 | 9/2011 | Lau et al. |

FOREIGN PATENT DOCUMENTS

| | | |
|---|---|---|
| EP | 1 037 447 A3 | 10/2001 |
| JP | 11-64482 | 3/1999 |
| JP | 11-258325 | 9/1999 |
| JP | 11-289574 | 10/1999 |
| JP | 11-306491 | 11/1999 |
| WO | WO 97/14054 | 4/1997 |
| WO | WO 97/41654 A1 | 11/1997 |
| WO | WO 98/01769 A1 | 1/1998 |
| WO | WO 98/16045 A1 | 4/1998 |
| WO | WO 98/40837 | 9/1998 |
| WO | WO 00/51391 A1 | 8/2000 |
| WO | WO 01/50151 A1 | 7/2001 |
| WO | WO 01/63318 A1 | 8/2001 |
| WO | WO 01/75700 A2 | 10/2001 |
| WO | WO 02/42979 A1 | 5/2002 |
| WO | WO 02/084618 A1 | 10/2002 |
| WO | WO 03/012720 A1 | 2/2003 |

OTHER PUBLICATIONS

Office Action for U.S. Appl. No. 10/397,474, dated Feb. 27, 2007.
Office Action for U.S. Appl. No. 10/397,474, dated Sep. 6, 2007.
Notice of Allowance for U.S. Appl. No. 10/397,474, dated Mar. 28, 2008.
Restriction Requirement for U.S. Appl. No. 12/214,434, dated Nov. 16, 2010.
Office Action for U.S. Appl. No. 12/214,434, dated Dec. 7, 2010.
Notice of Allowance for U.S. Appl. No. 12/214,434, dated Feb. 9, 2011.
Office Action for U.S. Appl. No. 13/113,972, dated Aug. 11, 2011.
Notice of Allowance for U.S. Appl. No. 13/113,972, dated Nov. 28, 2011.
Notice of Allowance for U.S. Appl. No. 13/113,972, dated Apr. 4, 2012.
"352C22 Miniature Low Profile ICP Accelerometer," Precision Accelerometers, PCB Piezoelectronics Products—SVS Division, webpages, pp. 1-2 (downloaded Apr. 11, 2002: www.pcb.com/products/svs/svs352c22.html).
"3G Mobile Internet Revolution, . . . only with Location Based Services!" pp. 1, (downloaded Aug. 10, 2002: http://webhome.idirect.com/~dental/3glocator/home.htm).
"Airline Cargo Containers," Case Study, RJI Incorporated, webpages, pp. 1-2 (downloaded Mar. 16, 2002: www.rji.cc/casestudies/airlinecargocontainers.html).

"Airline Food Carts," Case Study, RJI Incorporated, webpages, pp. 1-2 (downloaded Mar. 16, 2002: www.rji.cc/casestudies/airlinefoodcarts.html).

"An Introduction to SnapTrack Server-Aided GPS Technology," SnapTrack Inc., Apr. 3, 2007.

Archived page entitled "Money-Back Guarantee Policy" from fedex.com, archived by the Internet Archive on Aug. 17, 2000.

"Audiovox Intros GPS, Bluetooth Phone;" INT Media Group, Inc. (allNetDevices), Apr. 5, 2002. (downloaded:www.allnetdevices.com/wireless/news/2001/1/15/audiovox_intros. html).

"Carrier and end-user applications for wireless location systems," TruePosition, Inc., pp. 1-7.

"Danger -Products" and "Hiptop Communicator Brochure," Danger, Inc., downloaded Oct. 26, 2003: www.danger.com/products.php).

"Developing a GPSs for the Global Supply Chain," Aberdeen Group, Inc., Executive White Paper, Jun. 2002.

"Devices for Text Messages in Deutsche Telekom's fixed network have already found their way into many households," Deutsche Telekom AG, Press Release, Mar. 13, 2002, pp. 1-2.

"Digital/Analog Compass Sensors" and "1655 Digital Compass Sensor," webpages, The Robson Company, Inc., pp. 1-2 (downloaded Apr. 11, 2002: www.dinsmoresensors.com/index.html).

"EarthTrack™ Vehicle Tracking Systems," Outfitter Satellite, Inc., 1998 (downloaded Jan. 22, 2000).

"Enhanced Tracking," United Parcel Service of America, Inc. (UPS), webpages, pp. 1-2 (downloaded Jun. 1, 2002: www.ups.com/myupsinfo/info/etrack?pnav=stdservice).

"Fleet Management Systems-Asset Tracking Devices," Axiom Navigation Inc., 2000-2001 (downloaded Oct. 19, 2002: www.axiomnav.com/Prod_Systems/prod_system.asp).

"Frozen Food Warehouse," Case Study, RJI Incorporated, webpages, pp. 1-3 (downloaded Mar. 16, 2002: www.rji.cc/casestudies/frozenfoodwarehouse.html).

"FunMail Launches on the NTT DoCoMo i-mode network," FunMail, Press Release, May 1, 2001, pp. 1-2.

"Global Cell Phone Location," Axiom Navigation Inc., 2000-2001 (downloaded Oct. 19, 2002: www.axiomnav.com/Prod_Global/prod_global.asp).

"Global Locating Services," SkyBitz, webpage, p. 1, (downloaded Nov. 15, 2002: www.skybitz.com/services/gls.html).

"GLS Communicator," SkyBitz, webpages, pp. 1-2, (downloaded Nov. 15, 2002: www.skybitz.com/gls/communicator.html).

"Guide to Tracking Info.," Nippon Express, website page, p. 1 (downloaded Jun. 9, 2002: www.nittsu.co.jp/edoc/howtoe.htm).

"Introduction to SMS," by C. Tull of Anywhere YouGo.com, pp. 1-4 (downloaded:www.devx.com/wireless/articles/SMS/SMSintro-asp).

"IO Data Develops GPS Adapter for I-Mode Mobile," AsiaBizTech, Sep. 17, 2002, pp. 1-2.

"Locate Networks: Our Service," Locate Networks, webpages, pp. 1-7 (downloaded Sep. 26, 2002: www.locatenetworks.com/).

"MMS phones: Don't believe the hype," CNN.com/SCI-TECH, Aug. 8, 2002, pp. 1-3.

"Mobile Location Based Services: Cell Tracking Devices of People & Thongs . . . ," pp. 1-2, (downloaded Aug. 10, 2002: http://3glocate.com).

"MoniTrack," Case Study, RJI Incorporated, webpages, pp. 1-2 (downloaded Mar. 16, 2002: www.rji.cc/technology/telematic.html).

"My UPS.COM Benefits," United Parcel Service of America, Inc. (UPS), webpage, p. 1 (downloaded Apr. 13, 2002: www.ups.com/myupsinfo/info/benefits?pnav=stdsservice).

"NavMate® Navigation System," Visteon Corporation, webpage, pp. 1-2 (downloaded Jun. 21, 2002: www.visteon.com/technology/automotive/navmate.html).

"News," SkyBitz, webpages, pp. 1-8, (downloaded Nov. 15, 2002: www.skybitz.com/about/news.html).

"Pakhound: Your Watchdog in the Shipping Industry," website pages, pp. 1-3 (downloaded Jun. 9, 2002: www.pakhound.com/fact.asp).

"Parkwatch and Wherenet Unveil the First Amusement Visitor Locating system," ParkWatch, Press Release, Jun. 27, 2000.

"pulver.com's Location Based Services Report," pulver.com, Inc., Oct. 2001, pp. 1-17 (downloaded Jun. 4, 2002: www.pulver.com/lbsreport/lastbsreport.02/oct01.txt).

"Radio Frequency Identification (RFID)," Case Study, RJI Incorporated, webpage, p. 1 (downloaded Mar. 16, 2002: www.rji.cc/technology/rfid.html).

"Real Time Location System (RTLS)," Case Study, RJI Incorporated, webpage, p. 1 (downloaded Mar. 16, 2002: www.rji.cc/technology/rtls.html).

"Real-Time Warehouse Tracking," Case Study, RJI Incorporated, webpages, pp. 1-2 (downloaded Mar. 16, 2002: www.rji.cc/casestudies/rtwarehousetracking.html).

"Savi Reusable Transport Container," Savi Technology, Inc., Apr. 30, 2002, pp. 1-2.

"Send images to i-mode phones," Mobile Media Japan, 2001, pp. 1-3.

"Ski Rental with Auto ID and Tracking," Case Study, RJI Incorporated, webpages, pp. 1-2 (downloaded Mar. 16, 2002: www.rji.cc/casestudies/skirentalcompany.html).

"SnapTrack and SignalSoft Corp. Team Up to Trial Location-based Information Service for GSM Test Group," Press Release, SnapTrack Inc., Dec. 6, 1999.

"SnapTrack Awarded Additional Key Patents for Enhanced GPS System," Press Release, SnapTrack Inc., Jan. 4, 2000.

"Start-up crams single chip with phone, GPS and Bluetooth," CNET Network, Inc. (ZDNET), Mar. 22, 2002 (downloaded: http://news.zdnet.co.uk/story/0,t284-x2107163,00.html).

"Status Icons/Messages," Yahoo! Messenger Help, Yahoo! Inc., 2002, pp. 1-2.

"Technical Applications of Our Current Technology," Aetherwire, webpages, pp. 1-4 (downloaded Mar. 16, 2002: www.aetherwire.com/CDROM/General/appl1.html).

"The Always on Network," Position Paper, Nortel Networks, 2002.

"Theme Park Visitors & Cashless Purchasing," Case Study, RJI Incorporated, webpages, pp. 1-2 (downloaded Mar. 16, 2002: www.rji.cc/casestudies/themepark.html).

"Track Shipments—Detailed Results," FedEx, webpages, pp. 1-2 (downloaded Oct. 29, 2002: www.fedex.com).

"Track Your FedEx Shipments via Email," FedEx, webpages, pp. 1-2 (downloaded Oct. 29, 2002: www.fedex.com).

"Tracking Helpful Tips," United Parcel Service of America, Inc. (UPS), webpages, pp. 1-2 (downloaded Jun. 1, 2002: www.ups.com/tracking/nm_help.html).

"Trimble and Rosum Team to Develop Universal Positioning Technology," Trimble Navigation, Inc., News Release, Feb. 27, 2003.

"Turning Position Into Knowledge," SkyBitz, webpage, p. 1, (downloaded Nov. 15, 2002: www.skybitz.com).

"UPS Package Tracking," United Parcel Service of America, Inc. (UPS), webpages, pp. 1-2 (downloaded Apr. 13, 2002: www.ups.com/tracking/tracking.html).

"UPS Wireless Solutions," United Parcel Service of America, Inc. (UPS), webpage, p. 1 (downloaded Apr. 13, 2002: www.ups.com/myupsinfo/info/wireless?pnav=stdsservice).

"Welcome to Iship, Inc.," iShip, Inc., webpages, pp. 1-2, (downloaded Jun. 9, 2002: www.iship.com/).

"Welcome to Traker Systems," Tracker Systems, webpages, pp. 1-2 (downloaded Jun. 9, 2002: www.trakersystems.com).

"What are Instant Messages?" Yahoo! Messenger Help, Yahoo! Inc., 2002, pp. 1.

"What is "3G" technology?," CNN.com/SCI-TECH, Oct. 22, 2001, pp. 1-3.

"What is a Friend List?" Yahoo! Messenger Help, Yahoo! Inc., 2002, pp. 1.

"Wherify Wireless and SiRF Team to Deliver Child Locator System," Wherify Wireless, Inc., Press Release, Mar. 19, 2001, pp. 1-2.

"Wherify Wireless Breakthrough in Location-Based Services," Mobilemag.com, Feb. 28, 2001, p. 1.

"Wherify Wireless GPS Locator for Kids User Guide," Wherify Wireless, Inc., 2003, pp. 1-106.

"Wherify Wireless Location Services," Wherify Wireless, Inc., webpages, pp. 1-5 (downloaded: Mar. 25, 2003: www.wherifywireless.com/prod_watches.htm).

"X-GPS™—Hybrid GPS Location Server Solution," Axiom Navigation Inc., 2000-2001 (downloaded Oct. 19, 2002: www.axiomnay.com/Prod_Global/x-gps.asp).

"Yahoo! Messenger—Sending Messages to a Mobile Phone," Yahoo! Messenger, Yahoo! Inc., 2002, pp. 1-7 (downloaded Oct. 27, 2002: http://messenger.yahoo.com/messenger/wireless/pc2sms/tour1.html(through /tour7.html)).
"Yahoo! Messenger for Text Messaging," Yahoo! Messenger, Yahoo! Inc., 2002, pp. 1-10 (downloaded Oct. 27, 2002: http://messenger.yahoo.com/messenger/wireless/smsmsgr/tour1.html (through /tour7.html)).
"Yahoo! Messenger for WAP," Yahoo Messenger, Yahoo! Inc., 2002 (tours 1-9), pp. 1-17 (downloaded Oct. 27, 2002: www.messenger.yahoo.com/messenger/wireless/wap/tour1.html(through /tour9.html)).
Accelerometers—General Purpose, LP Series, Crossbow Technology, Inc., data sheet, pp. 1-3 (downloaded Apr. 11, 2002: www.xbow.com/Products/Accelerometers.htm).
Bickers, "Eyes in the sky," SafeTzone Technology Corporation, webpages, 2001, pp. 1-3 (downloaded: www.safetzone.com/newsKiosk.asp).
Chertkoff, Rachel, "Vehicle Locator Systems," Pager Technology, pp. 1-2, 1998.
Commercial Uses for LoJack (webpage), LoJack Corporation, downloaded Jan. 22, 2000.
Crossbow Product Guide—Accelerometers, Crossbow Technology, Inc., webpages, pp. 1- 3 (downloaded Apr. 11, 2002: www.xbow.com/Products/Accelerometers.htm).
Delphi and MobileAria Demonstrate True Hands Free In-Vehicle Mobile Productivity Services At CES, Press Release, Delphi Automotive Systems, Jan. 8, 2002 (downloaded Apr. 5, 2002: www.delphiauto.com/news/pressRelease/pr6828-01082002).
F. Rivera, "Special Report: Keeping Tabs on Your Teen," 7 News, Boston, Apr. 30, 2002, pp. 1-3.
FedEx Insight, FedEx, webpages, pp. 1-11 (downloaded Oct. 29, 2002: www.fedex.com).
GPS2000, Omega Research and Development, Inc., webpages, pp. 1-9 (pp. 7-9 pertain to an online tour) (downloaded Jul. 14, 2003: www.gps2000online.com/).
IMVironment, Yahoo! Messenger Yahoo! Inc., 2002, pp. 1-12 (downloaded (including) Oct. 27, 2002: http://help.yahoo.com/help/us/mesg/imv/imv-01.html(through/index5.html).
J.Wrolstad, "Chrysler Claims First With Bluetooth Mobile Phone System," Wireless Newsfactor, Oct. 26, 2001.
K. Hill, "Prada Uses Smart Tags to Personalize Shopping," CRMDaily.com, Apr. 24, 2002, pp. 1-4.
K. Miyake, "Sharp to unveil 3G PDA-type cell phone," ITworld.com, Inc., Jan. 11, 2002.
Kleinknecht, William, "Juvenile authorities want satellite tracking for felons," The Star-Ledger Ledger of New Jersey, Nov. 18, 1997.
LoadTrak, pp. 1-2 (downloaded Jun. 4, 2002: www.load-trak.com).
Marek, "The Unstoppable SnapTrack," Wireless Week, Dec. 18, 2000.
Motorola Consumer Catalog: Pagers (webpage), Motorola, Inc., downloaded Jan. 19, 2000.
My.Roadway! Roadway Express, Inc., webpages, pp. 1-2, (downloaded Jun. 9, 2002: www.quiktrak.roadway.com/cgi-bin/quiktrak).
Packtrack™, PackTrack.com, webpages, pp. 1-2 (downloaded Jun. 9, 2002: www.packtrack.com).
Precision Accelerometers, PCB Piezoelectronics Products—SVS Division, webpages, pp. 1-2 (downloaded Apr. 11, 2002: www.pcb.com/products/svs/index.html).
Rabinowitz and Spilker, Jr., "A New Positioning System Using Television Synchronization Signals," Rosum Corporation, pp. 1-11 (downloaded May 21, 2003).
Rabinowitz and Spilker, Jr., "Positioning Using the ATSC Digital Television Signal," Rosum Corporation Whitepaper, Rosum Corporation (downloaded May 21, 2003).
Real Time Locating System, Executive Summary, Technology Systems International, Inc., 2007.
Ryan, "Catching up with Dick Tracy," San Francisco Chronicle, news article, Mar. 18, 2002.
SandPiper GPS Receiver, Specification sheet by Axiom Navigation Inc. (www.axiomnav.com) 2006.
Smart Antenna, Specification sheet by Axiom Navigation Inc. (www.axiomnav.com) 2008.
SnapTrack—Privacy Protection (webpage), SnapTrack Inc., downloaded Jan. 19, 2000.
SnapTrack—Technology At Work (webpage), SnapTrack Inc., downloaded Jan. 19, 2000.
SnapTrack in Action (webpage), SnapTrack Inc., downloaded Jan. 19, 2000.
Stilp, Louis A., "Examining the Coming Revolution in Location Services," pp. 1-11.
Strom, Stephanie. "A Wild Sleigh Ride at Federal Express," The New York Times, Dec. 20, 1994.
Swift A2 GPS Receiver, Specification sheet by Axiom Navigation Inc. (www.axiomnav.com) 2010.
Swift B2 GPS Receiver, Specification sheet by Axiom Navigation Inc. (www.axiomnav.com) 2010.
TruePosition Virtual Brochure (webpage), TruePosition, Inc.
Wong, "Fishers, golfers join the rush to GPS," San Jose Mercury News, news article, Mar. 25, 2002.
Danger Product Overview, 5 pgs., Danger, Inc.
PCV*trak*™ Installation and Operator's Manual, Trimble Navigation, 24623-00 Rev. A, May 1994, pp. 1-259.
"Advanced Traveler Aid Systems for Public Transportation," Final Report, Federal Transit Administration, Sep. 1994, pp. 1-131.
Campbell, Laurel, "Security—Military satellite enlisted to thwart car crime," The Commercial Appeal, Sep. 26, 1996, pp. 5B.
Law, Alex, "Week in Wheels/ . . . From a Driver's Notebook," Newsday, Inc., Sep. 20, 1996, pp. C03.
Cortez, Angela, "Springs police can track thief, vehicles," The Denver Post, Sep. 10, 1996, pp. B-01.
"OnGuard Tracker Nabs Auto Burglar," Global Positioning & Navigation News, vol. 6, No. 16, Aug. 8, 1996.
"OnGuard Tracker Nabs Auto Burglar," Section: Financial News, PR Newswire, Jul. 29, 1996.
Nauman, Matt, "Pressing the Panic Button: Car Security Enters a New Age with Cellular Phones and Satellites that Watch Over You," San Jose Mercury News, Jun. 21, 1996, pp. 1G.
"Monday Briefing" San Antonio Express-News, p. 1, Part B, Jun. 10, 1996.
"OnGuard Tracker Makes Debut on 'One Lap of America'," PR Newswire, Jun. 7, 1996.
"OnGuard Tracker Makes Debut on 'One Lap of America'," Southwest Newswire, Jun. 7, 1996.
Dominguez, Raul, "Women get their day in sun—American Golf planning events nationwide May 18," San Antonio Express-News, Apr. 18, 1996, pp. 2, part B.
"Vehicle Navigation Units Being Measured in Luxury Autos," Global Positioning & Navigation News, vol. 6, No. 7, Apr. 4, 1996.
"Advanced Business Sciences, Inc. Announces Completion of Acquisition of Comguard of Illinois," Business Wire, Aug. 26, 1998.
"Advanced Business Sciences, Inc. Announces Filing With Securities and Exchange Commission," Business Wire, Jun. 25, 1999.
"Advanced Business Sciences, Inc. Announces Preliminary Fourth Quarter 1998 Revenue Results," Business Wire, Feb. 4, 1999.
"Business People Burnsy's Grill Names Two," Omaha World-Herald, Section Business, p. 4M, Oct. 20, 1996.
"Company Sees Prisoner Tracking and Monitoring Market Niche," Global Positioning & Navigation News, vol. 6, No. 10, May 16, 1996.
GPS-Based Personal Monitoring Systems Offered to Corrections, Private Market, Global Positioning & Navigation News, vol. 8, No. 11, Jun. 3, 1998.
GPS tracks parolees, probationers, Corrections Professional, vol. 5, No. 6, Nov. 19, 1999.
High-Tech System Tracks Offenders—Satellites Watching Criminals, Business Wire, Nov. 14, 1997.
Briefs, Global Positioning & Navigation News, vol. 9, No. 4, Feb. 24, 1999.
Dunkelberger, Lloyd, "Lawmakers question criminal-tracking system," Sarasota Herald-Tribune (Florida), pp. 16A, Nov. 28, 1999.
Powell, Barbara. "New gadgets help drivers find their way," Fort Worth Star-Telegram (Texas), p. 1, Jan. 20, 1997.
"New Service Lets Corrections Agencies Track Offenders by Satellite," PR Newswire, Jan. 11, 1999.
"New Service Lets Corrections Agencies Track Offenders by Satellite; SecurityLink Offers "GPS" Tracking for Offenders on Electronic Monitoring—Sandusky Municipal Court Adopts Technology for Local Offenders," PR Newswire, Jan. 12, 1999.
"New Service Lets Corrections Agencies Track Offenders by Satellite; SecurityLink Offers 'GPS' Tracking for Offenders on Electronic Monitoring," PR Newswire, Section: Financial News, Jan. 11, 1999.
"New Service Lets Corrections Agencies Track Offenders by Satellite," Satellite Today, vol. 2, No. 8, Jan. 13, 1999.
"Prisoner Security Monitoring Company Grabs Contracts for GPS-Based System," Global Positioning & Navigation News, vol. 7, No. 1, Jan. 15, 1997.
Atwater, Andi, "Proposal seeking 24-hour tracking of all sex offenders," The News-Press (Fort Meyers, FL), pp. 1A, Feb. 20, 2000.
Briefs, Global Positioning & Navigation News, vol. 9, No. 3, Feb. 10, 1999.
Brauer, David, "Satellite 'Big Brother' Tracks Ex-Inmates; Agencies Experiment with GPS to Monitor Parolee Whereabouts," Chicago Tribune, Section: News, p. 31, Dec. 18, 1998.
"Satellite Spotlight; Eye in the Sky to Monitor Parolees," Satellite News, vol. 21, No. 15, Apr. 13, 1998.
"Satellite Spotlight: Fighting Crime From Space," Satellite News, vol. 19, No. 20, May 13, 1996.
Prohaska, Thomas J, "Satellite Will Keep Tabs on Convicts," Buffalo News (New York), Section: Local, p. 5B, Sep. 20, 1999.
"Sierra Wireless and Pro Tech Team Up on Monitoring Product," Global Positioning & Navigation News, vol. 8, No. 8, Apr. 22, 1998.
Anderson, Larry, "Technology rules at Securing New Ground," Access Control & Security Systems Integration, Section: Industry Outlook; ISSN 1084-6425, Dec. 1999.
Trimble Navigation Warns 2nd-Quarter Earnings to Miss Target, Dow Jones Business News, Jul. 10, 1998.
"Trimble Navigation's Net Income Skidded 93% Amid Order Delays," Dow Jones Business News, Jul. 23, 1998.
Briefs, Global Positioning & Navigation News, vol. 9, No. 2, Jan. 27, 1999.
Briefs, Global Positioning & Navigation News, vol. 9, No. 14, Jul. 14, 1999.
Dailey et al. "Automatic Transit Location System," Final Research Report, 55 pgs., Feb. 1996.
Maguire, Jr. et al. "SmartBadges: a wearable computer and communication system," codes/CASHE '98, 47 pgs., 1998.
Koshima et al. "Personal locator services emerge," IEEE Spectrum, Feb. 2000, pp. 41-48.
Zygowicz et al. "State of the Art in Automatic Vehicle Location Systems," Center for Urban Transportation Studies, University of Wisconsin, Milwaukee, Feb. 1998.
Ashworth, Jon. "Big brother is watching you," The Times (London), Section: Features, May 7, 1999.
"Car Thieves Take the "Bait" in Michigan; Two Suspects Reeled in With OnGuard," Business Wire, Sep. 11, 1997.
Sauer, Matthew, "Company Finds Niche by Giving Directions . . . " Sarasota Herald-Tribune (Florida), Section: Business Weekly, p. 1, Jul. 7, 1997.
"ATX Technologies Signs Nationwide Service Deal with AT&T," Global Positioning & Navigation News, vol. 7, No. 9, May 7, 1997.
"Car Thieves Take the 'Bait' in Tulsa; Two Suspects Caught Off Guard with OnGuard Once Again," PR Newswire, Section: Financial News, Jan. 8, 1997.
"Car Thieves Take the 'Bait' in Tulsa; Two Suspects Caught Off Guard with on Guard," PR Newswire, Section: Financial News, Dec. 9, 1996.
Jackson, Terry, "Smart Cars Whether by Satellite or the Internet, High-Tech Devices and Services May Make Crumpled Road Maps a Thing of the Past," The Miami Herald, Section: Travel, p. 1J, Oct. 6, 1996.
"San Antonio Personal Security Company Links Up with Senior PGA Golfer," PR Newswire, Section: Financial News, Apr. 1, 1996.
"San Antonio Personal Security Company Links Up with Senior PGA Golfer," Southwest Newswire, Apr. 1, 1996.
Business Briefs, San Antonio Express-News, Mar. 25, 1996.
"ATX Research Signs Exclusive Sales Agreement with Arizona Company," PR Newswire, Mar. 21, 1996.
"ATX Research Signs Exclusive Sales Agreement with Arizona Company," Southwest Newswire, Mar. 21, 1996.
"Automotive GPS Satellite/Safety System Race Is On," Southwest Newswire, Feb. 20, 1996.
"Dealerships Can Track Down New Aftermarket Revenues," PR Newswire, Feb. 9, 1996.
"ATX Research Unveils New Stealthtrac Capability," PR Newswire, Feb. 9, 1996.
"Dealerships Can Track Down New Aftermarket Revenues," Southwest Newswire, Feb. 9, 1996.
Briefs, Global Positioning & Navigation News Wire, vol. 6, No. 2, Jan. 24, 1996.
"ATX Research Provides Police Departments With Onguard Personal Security and Vehicle Tracking System," PR Newswire, Jan. 15, 1996.
"ATX Research Provides Police Departments With Onguard Personal Security and Vehicle Tracking System," Southwest Newswire, Jan. 15, 1996.
"ATX Research Relocates to New Corporate Headquarters," PR Newswire, Dec. 12, 1995.
"ATX Research Relocates to New Corporate Headquarters," Southwest Newswire, Dec. 12, 1995.
"Texas invention tracks stolen cars, lets driver call for help," The Vancouver Sun, Oct. 20, 1995.
"San Antonio Company Unveils Satellite/Cellular Personal Security System," PR Newswire, Oct. 3, 1995.
"San Antonio Company Unveils Satellite/Cellular Personal Security System," Southwest Newswire, Oct. 3, 1995.
Culler et al., *MICA: The Commercialization of Microsensor Motes*, Sensors, vol. 19, No. 4 (Apr. 1, 2002).
Darabi et al., *A 2.4-GHz CMOS Transceiver for Bluetooth*, IEEE Journal of Solid-State Circuits, vol. 36, No. 12 (Dec. 2001).
J. Fraden, Handbook of Modern Sensors, Springer-Verlag (1996).
Grimes, Craig A., et al., *Wireless Magnetoelastic Resonance Sensors: A Critical Review*, Sensors (Jul. 23, 2002).
Helfenstein et al. Circuits and Systems for Wireless Communications, Kluwer Academic Publishers (2000).
Hill et al., *System Architecture Directions for Networked Sensors*, ACM/ASPLOS-IX (Nov. 2000).
Madou, Marc J., Fundamentals of Microfabrication, CRC Press (2002).
Mainwaring et al., *Wireless Sensor Networks for Habitat Monitoring*, ACM (Sep. 28, 2002).
Razavi, Behzad, RF Microelectronics, Prentice Hall (1998).
Rofougaran et al., *A Single-Chip 900-MHz Spread-Spectrum Wireless Transceiver in 1-μm CMOS-Part II: Receiver Design*, IEEE Journal of Solid-State Circuits, vol. 33, No. 4 (Apr. 1998).
Senturia, Stephen D., Microsystem Design, Kluwer Academic Publishers (2001).
Steyaert et al., "A 2-V CMOS Cellular Transceiver Front-End," *IEEE Journal of Solid-State Circuits*, vol. 25, No. 12, Dec. 2000, pp. 1895-1907.

* cited by examiner

METHOD AND SYSTEM FOR ENHANCED MESSAGING

CROSS REFERENCE TO RELATED APPLICATIONS

This application is a continuation of U.S. patent application Ser. No. 13/113,972, filed May 23, 2011, and entitled "METHOD AND SYSTEM FOR ENHANCED MESSAGING" (now U.S. Pat. No. 8,176,135), which is hereby incorporated by reference, which in turn is a continuation of U.S. patent application Ser. No. 12/214,434, filed Jun. 19, 2008, and entitled "METHOD AND SYSTEM FOR ENHANCED MESSAGING" (now U.S. Pat. No. 7,953,809), which is hereby incorporated herein by reference, which in turn is a continuation of U.S. patent application Ser. No. 10/397,474, filed Mar. 26, 2003, and entitled "METHOD AND SYSTEM FOR ENHANCED MESSAGING" (now U.S. Pat. No. 7,403,972), which is hereby incorporated herein by reference, and which in turn claims benefit of: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

This application is also related to: (i) U.S. patent application Ser. No. 10/397,473, filed Mar. 26, 2003, and entitled "METHOD AND APPARATUS FOR INTELLIGENT ACQUISITION OF POSITION INFORMATION (now U.S. Pat. No. 6,975,941);" (ii) U.S. patent application Ser. No. 10/397,472, filed Mar. 26, 2003, and entitled "METHODS AND APPARATUS TO ANALYZE AND PRESENT LOCATION INFORMATION (now U.S. Pat. No. 7,218,938);" (iii) U.S. patent application Ser. No. 10/397,637, filed Mar. 26, 2003, and entitled "METHOD AND SYSTEM FOR PROVIDING SHIPMENT TRACKING AND NOTIFICATIONS (now U.S. Pat. No. 7,212,829);" (iv) U.S. patent application Ser. No. 10/397,641, filed Mar. 26, 2003, and entitled "METHOD AND SYSTEM FOR PERSONALIZED MEDICAL MONITORING AND NOTIFICATIONS THEREFOR (now U.S. Pat. No. 7,905,832);" (v) U.S. patent application Ser. No. 10/397,640, filed Mar. 26, 2003, and entitled "INEXPENSIVE POSITION SENSING DEVICE (now U.S. Pat. No. 7,321,774);" (vi) U.S. patent application Ser. No. 10/397,512, filed Mar. 26, 2003, and entitled "APPLICATIONS OF STATUS INFORMATION FOR INVENTORY MANAGEMENT."

BACKGROUND OF THE INVENTION

1. Field of the Invention

The present invention relates to communication devices and, more particularly, to enhanced messaging for communication devices.

2. Description of the Related Art

Today, electronic mail (email) is a common mode of communication. One person, acting as a sender, composes an email message and then sends the email message to another person designated as a recipient. The sender composes the email message by interacting with a communication device. The recipient is able to read the email message by interacting with another communication device. Communication devices are often personal computers or mobile telephones. These communication devices can receive and transmit electronic mail messages over a network. The network can be public or private as well as wired or wireless.

Although email is an effective means of communication, when a sender is using a mobile telephone, composing an email message can be tedious and difficult. User interfaces can provide limited assistance to users such as by creating email messages through word prediction, predetermined responses, etc. Nevertheless, given the difficulties with composing messages, email messages from mobile telephones in most cases are relatively short. Recently, communication devices, including mobile telephones, have been able to send and receive instant messages, which are short text messages sent and received in near real time between communication device.

Apart from sending and receiving email messages, mobile telephones can also display the location or availability (i.e., online or offline) of other users via their mobile telephones. This information is provided by a wireless service provider that monitors location or availability of users via their mobile phones. Unfortunately, such information needs the assistance of wireless service providers and tends not to be widely available. Moreover, if such information is available, the information would very likely not be current and thus the usefulness of the information would be limited.

Thus, there is a need for improved approaches to enhance the capabilities of messaging.

SUMMARY OF THE INVENTION

Broadly speaking, the invention relates to techniques for acquiring, sending, receiving or using status information from a remote location over a network. The status information is transmitted by electronic devices over the network. The status information can be provided by one or more sensors associated with the electronic device that is transmitting the status information. The status information can be transmitted with messages so as to enhance the messages.

According to one aspect of the invention, base messages are entered by a user or automatically produced. The base messages can be text messages (including instant messages), voice messages, video messages or other types of messages. The base messages are augmented to additionally include status information, such as position and/or other conditions information. The status information is normally provided by one or more sensors. In one implementation, base messages can be combined with status information, whereby the resulting messages are referred to as enhanced messages. These enhanced messages are electronically sent from and received at electronic devices, such as personal computers and mobile communication devices.

The invention can be implemented in numerous ways including, a method, system, device, graphical user interface, and a computer readable medium. Several embodiments of the invention are discussed below.

As a method to facilitate communication among users of mobile electronic devices user communication system for communicating between users of mobile communication devices, one embodiment of the invention can, for example, include at least the acts of: receiving message content for a text message via the first mobile electronic device; acquiring status information of the first mobile electronic device, the status information including at least position information associated with the first mobile electronic device; determining a plurality of other mobile electronic devices or users thereof that are authorized to receive the message content and the status information; determining whether at least one user selection has been provided via the first mobile communication device to indicate whether the status information is to be provided with the text message, and initiating sending of the text message including the message content along with the status information to each of the plurality of other mobile electronic devices via a wireless network, provided that it is determined that the status information is to be provided with the text message and provided that the plurality of other mobile electronic devices or users thereof are authorized to receive the text message and the status information.

As a method for providing communications between computing devices, another embodiment of the invention includes at least the acts of: obtaining a message at a first mobile communication device to be delivered to a second mobile communication device; determining whether status information is to accompany the message; sending the message without any status information when it is determined that status information is not to accompany the message; and acquiring status information at the first mobile communication device and then sending the message and the status information to the second mobile communication device when it is determined that status information is not to accompany the message.

As a method for displaying a message on a display device of a computing device, one embodiment of the invention includes at least the acts of: receiving a message from another computing device over a network; determining whether the message includes at least status information; extracting the status information from the message when it is determined that the message includes at least the status information; and displaying the message and at least one representation of the status information on the display device following the extracting when it is determined that the message includes at least the status information.

As a method for displaying a message on a display device of a computing device, another embodiment of the invention includes at least the acts of: receiving a message from another computing device over a network; determining whether the message includes at least status information; extracting the status information from the message when it is determined that the message includes at least the status information; and displaying the message and at least one representation of the status information on the display device following the extracting when it is determined that the message includes at least the status information.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

The invention relates to techniques for acquiring, sending, receiving or using status information from a remote location over a network. The status information is transmitted over the network between or among electronic devices. The status information can be provided by one or more sensors associated with the electronic device that is transmitting the status information. The status information can be transmitted with messages so as to enhance the messages. The electronic devices include at least computing devices, such as personal computers, personal digital assistants, pagers, and mobile telephones.

According to one aspect of the invention, messages are enhanced through use of status information. Base messages are entered by a user or automatically produced. The base messages can be text messages (including instant messages), voice messages, video messages or other types of messages. The base messages are augmented to additionally include status information, such as position and/or other conditions information. The status information is normally provided by one or more status sensors. In one implementation, base messages can be combined with status information, whereby the resulting messages are referred to as enhanced messages. These enhanced messages are electronically sent from and received at communication devices, such as personal computers and mobile communication devices.

Different embodiments of the invention are discussed below with reference to FIGS. 1-7. However, those skilled in the art will readily appreciate that the detailed description given herein with respect to these figures is for explanatory purposes as the invention extends beyond these limited embodiments.

According to one aspect of the invention, traditional messages transmitted between communication devices are augmented to additionally include status information, such as position and/or conditions information. The conditions information can pertain to one or more of environmental conditions, device-related conditions, or user-related conditions. One or more status sensors associated with the communication devices can capture or obtain the status information. In the case of position information, the status sensor can be a receiver, such as a Global Positioning System (GPS) receiver or other means.

Figure 1:
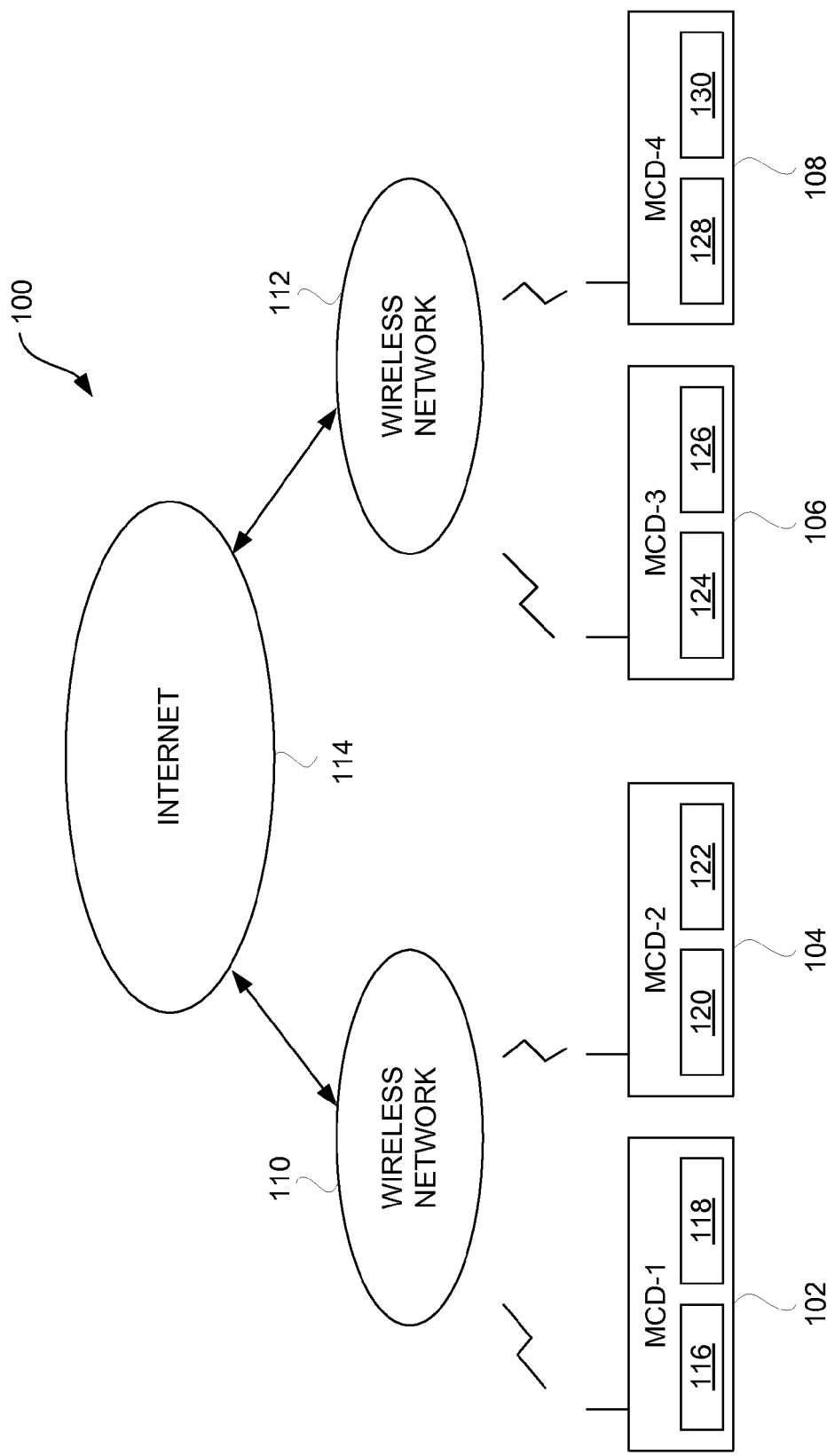
FIG. 1 is a block diagram of an enhanced messaging system according to one embodiment of the invention.

FIG. 1 is a block diagram of an enhanced messaging system 100 according to one embodiment of the invention. The enhanced messaging system 100 allows electronic messages (e.g., text messages) to be sent between mobile communication devices. The electronic messages being sent can be enhanced to include status information pertaining to (i) status of the associated mobile communication devices, (ii) status associated with the environment of the mobile communication devices, and/or (iii) status of the person(s) using the mobile communication device(s).

The enhanced messaging system 100 includes mobile communication devices 102, 104, 106 and 108. The mobile communication devices 102 and 104 communicate with a wireless network 110, and the mobile communication devices 106 and 108 communicate with a wireless network 112. The wireless networks 110 and 112 can be the same or different networks and can utilize same or different protocols. The wireless networks 110 and 112 can be coupled together and/or can couple to the Internet 114, and can support global messaging.

The enhanced messages are sent from one of the mobile communication devices to one or more other of the mobile communication devices. These enhanced messages can include additional information about the mobile communication device, its user and/or its environment. In one embodiment, the status information can include at least position (location) information and other status information. To provide the status information, the mobile communication devices 102, 104, 106 and 108 can include one or more status sensors, such as position detectors, and/or one or more other types of condition sensors for different conditions regarding the communication devices. A position detector can provide position information pertaining to its corresponding mobile communication device. Similarly, a condition sensor provides condition information pertaining to conditions sensed at the corresponding mobile communication device. More particularly, the mobile communication device 102 includes a position detector 116 and at least one condition sensor 118; the mobile communication device 104 includes a position detector 120 and at least one condition sensor 122; the mobile communication device 106 includes a position detector 124 and at least one condition sensor 126; and the mobile communication device 108 includes a position detector 128 and at least one condition sensor 130.

In one embodiment, the position information is obtained from a global positioning system (GPS) receiver, which can be in a mobile communication device. In other words, the position detector can be a GPS receiver. The position information can be obtained or augmented by a local positioning system such as utilized with a local network (e.g., Bluetooth, Wi-Fi, etc.). The conditions information can vary with application. Examples of conditions that can be provided within the conditions information include environment conditions or conditions of the environment of the corresponding mobile communication device. Environment conditions include temperature, humidity, pressure, gaseous or liquid states, chemical compositions, wind speed, color composition, scent, light, sound, smoke, particle or radiation (e.g., infrared radiation). The conditions information can be pertaining to a mobile communication device itself, such as force or pressure asserted on it, or its vibration, acceleration, speed (velocity) or direction. The conditions information can also include user-related conditions. These are conditions related to the user, who is typically a living being and who may be using the corresponding mobile communication device. Examples of user-related conditions include the being's physical conditions (e.g., heart beat, temperature, pupil dilation, hunger, perspiration, tired or sick), volitional behavior (e.g., facial expressions, jumping or moving), or the user's emotional state, such as the user's mood. Examples of emotional states or moods include sad, happy, mad, stressed, or excited. Some of these conditions are not determined directly by sensors, but are instead determined indirectly through processing other sensor data.

In one embodiment, an enhanced messaging system can operate in a distributed manner with little or no centralized management for status information exchange. In other words, the exchange of status information can be peer-to-peer (e.g., from one mobile communication device to another) without an intermediate centralized server to store and manage distribution of the status information. Such an embodiment can operate without assistance from wireless networks service providers. The enhanced messaging system 100 shown in FIG. 1 is suitable for use as such an embodiment.

In another embodiment, an enhanced messaging system can operate in a centralized manner, such as shown below in FIG. 2. In the case of a centralized system, or at least one providing centralized assistance, the status information can be stored and/or processed by a separate entity, independent of the parties sending and receiving information.

Figure 2:
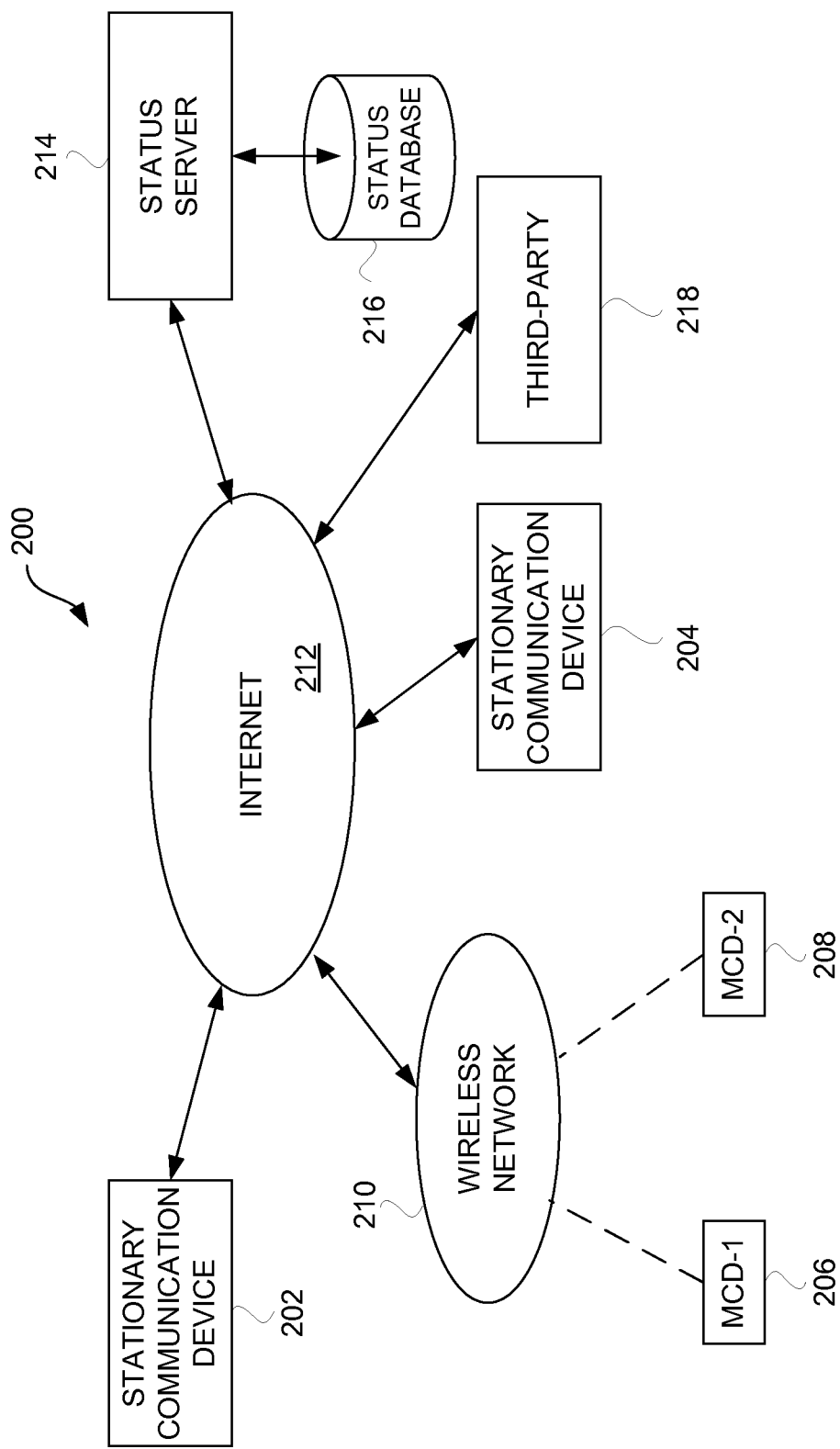
FIG. 2 is a block diagram of an enhanced messaging system according to another embodiment of the invention.

FIG. 2 is a block diagram of an enhanced messaging system 200 according to one embodiment of the invention. The enhanced messaging system 200 provides web-based enhanced messaging between users of communication devices. The enhanced messages being sent from one of the communication devices to one or more other of the communication devices. These enhanced messages can include additional information pertaining to a communication device, its user and/or its environment. In one embodiment, the status information can include at least position (location) information and conditions information.

According to the embodiment shown in FIG. 2, the enhanced messaging system 200 includes stationary communication devices 202 and 204. The enhanced messaging system 200 also includes mobile communication devices (MCD) 206 and 208. Typically, the mobile communication devices 206 and 208 are worn by, affixed to or carried by users. The enhanced messaging system 200 would normally be able to support multiple stationary communication devices, such as desktop computers, and mobile communication devices, such as mobile telephones, personal digital assistants and two-way pagers.

In general, messages can be transmitted (sent and/or received) between and/or among any of the communication devices, regardless of whether stationary or mobile. For discussion, it is assumed that a message is created and sent from the mobile communication device 206 to the stationary communication device 204. The message is assumed to be a text message, such as a real-time text message (e.g., instant message). In this example, the mobile communication device 206 acquires status information pertaining to the user, the device and/or the environment. The acquired status information is provided to the stationary communication device 204 along with the message.

The mobile communication devices 206 and 208 couple to a wireless network 210. The wireless network 210 couples to the Internet 212. Further, a status server 214 is coupled to the Internet 212. The status server 214 also couples to a status database 216. The Internet 212 can be replaced by other data networks (e.g., enterprise network, regional network, Local Area Network, Wide Area Network and global network).

The status information can include at least position (location) information and conditions information. The position information is obtained typically from a global positioning system (GPS) receiver within the first mobile communication device 206. The position information can be obtained or augmented by a local positioning system such as utilized with a local network (e.g., Bluetooth, Wi-Fi, etc.).

The conditions information can vary with application. Various examples of conditions that can be provided within the conditions information were noted above. The corresponding conditions sensor(s) can also be in the mobile communication device 206, or the sensor(s) can be wired or wirelessly coupled to the mobile communication device 206.

The status information that is obtained by the first mobile communication device 206 is sent by the first mobile communication device 206 to the status server 214 via the wireless network 210 and the Internet 212. The status server 214 stores the status information pertaining to the first mobile communication device 206 into the status database 216 such that it is associated with the first mobile communication device 206. The status server 214 monitors status information for numerous communication devices, including mobile communications devices and/or stationary communication device, and thus stores status information pertaining to numerous communication devices.

The enhanced messaging system 200 can also include at least one third-party 218. The third-party 218 is a user interested in status information acquired by mobile communication devices but does not normally receive the text messages also being sent.

The enhanced messaging system 200 can allow a recipient of the message to not only receive the text of the message but also the status information associated with the message. In one embodiment, the recipient receives the status information with the message. The recipient of the message can, for example, include one or more of the mobile communication devices 206 and 208 or one or more of the stationary communication devices 202 and 204, or users thereof. In another embodiment, an authorized party, such as the user of the stationary communication devices 202 and 204 or the third-party 218, can interact with the status server 214 through a web interface so that such users are able to access certain status information via the status server 214 and the status database 216. The web interface can facilitate a user in accessing status information anytime anywhere.

Figure 3:
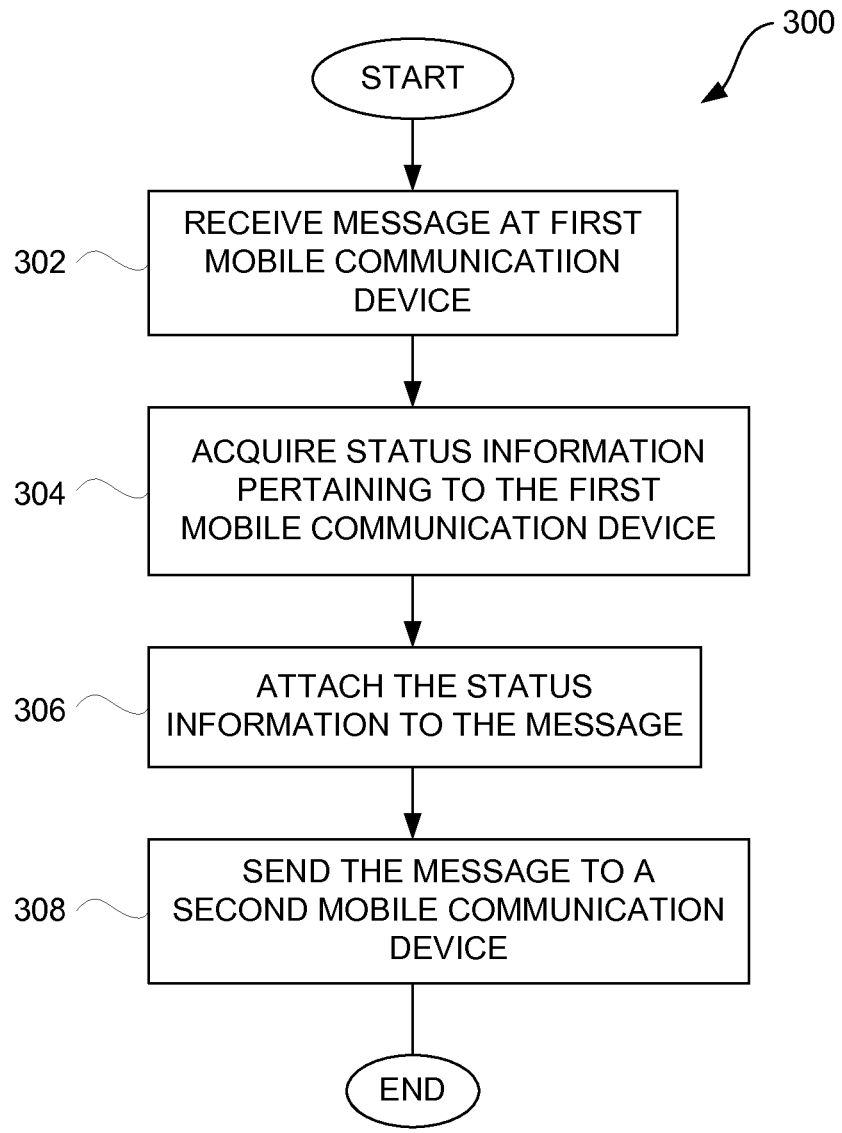
FIG. 3 is a flow diagram of status message processing according to one embodiment of the invention.

FIG. 3 is a flow diagram of status message processing 300 according to one embodiment of the invention. The status message processing 300 is, for example, performed by a mobile communication device (e.g., mobile telephone, two-way pager) or other computing device (e.g., desktop computer, gateway, server).

Initially, the status message processing 300 receives 302 a message at a first mobile communication device. For example, a user of the mobile communication device would typically interact with the mobile communication device (e.g., through a user interface) to create the message. Hence, in this embodiment, the message is considered to be a user-entered message. The user-entered message can be a voice message, a text message, a video message or some other type of input, or some combination thereof. A text message is, for example, a standard email message, a short message (e.g., SMS message) or an instant message. Status information pertaining to the first mobile communication device (and/or its user or environment) can be acquired 304. As noted above, in one embodiment, the status information can include at least position (location) information and/or conditions information. Some or all of the status information can then be attached 306 to the user-entered message. In one embodiment, at least some of the status information has been processed before attachment. The processed status information is still considered as status information. With the status information attached 306 to the user-entered message, the user-entered message becomes an enhanced message. The enhanced message is then sent 308 from the first mobile communication device to another electronic device, such as a second mobile communication device (e.g., mobile telephone, personal digital assistant, or pager) or other computing device (e.g., portable or stationary computer). Typically, the sending of the enhanced message involves electronic transmission of the enhanced message over a wireless network as well as perhaps a wired network. Although the enhanced message is often sent from one mobile communication device to another mobile communication device, the message can alternatively be sent to another computing device, such as a personal computer coupled to the network. Following the operation 308, the status message processing 300 is complete and ends.

Figure 4:
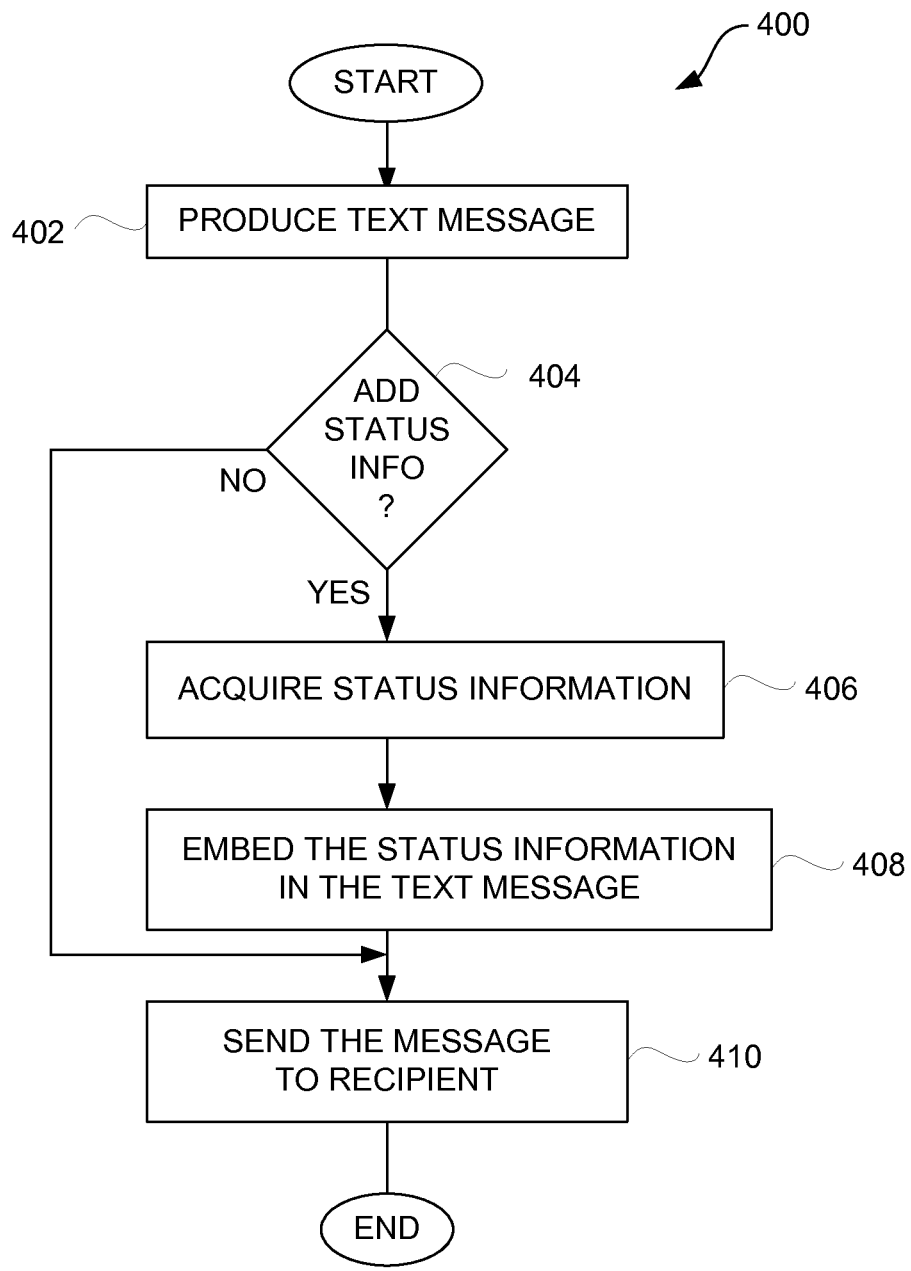
FIG. 4 is a flow diagram of send processing according to one embodiment of the invention.

FIG. 4 is a flow diagram of send processing 400 according to one embodiment of the invention. The send processing 400 is, for example, performed by a mobile communication device or other computing device.

The send processing 400 initially produces 402 a message. In this embodiment, the message is a user-entered message such as a text message. The text message can, for example, be produced or initiated by a user of the mobile communication device or other computing device. However, in other embodiment, the message can be a voice message or a video message.

A decision 404 then determines whether status information is to be added to the text message. The decision 404 allows the user to limit or restrict the status information that is sent to others. For example, the user might restrict the status information such that it can only be sent to authorized persons or destinations. The restrictions can be imposed by a profile or configuration information associated with the user. In one implementation, a user can make use of a list of recipients permitted to receive status information (e.g., pre-authorized recipients). As another example, a dialog box (or other graphical user interface) could be displayed to allow the user to select none, some or all of the available status information to be sent generally with all text messages, or specifically with a particular text message. As still another example, default authorizations can control the status information that is to be sent to recipients. Yet, in another example, status information can have different levels. Some levels can be more confidential than others, or some levels can be more important than others. These levels can also be set by the user. Regardless, different recipients can receive different levels of status information.

In any case, when the decision 404 determines that status information is to be provided with the text message, the status information is acquired 406. The status information is acquired from the mobile communication device or other computing device that is sending the text message. For example, the status information can be acquired 406 from a position detector and at least one condition sensor within (wired or wirelessly coupled to) the mobile communication device.

Regardless of how or when acquired, the status information can then be embedded 408 in the text message. Once the status information has been embedded in 408 (or otherwise combined with or linked to) the text message, the resulting message is referred to as an enhanced message. The status information can be embedded in an open (e.g., as additional displayed information) or hidden manner (e.g., as undisplayed text). In one example, the status information is embedded in the text message using a markup language. The status information being embedded in the text message can also be encrypted, or the entire enhanced message can be encrypted. After the status information is embedded 408 (as well as directly after the decision 404 when no status information is to be added, the resulting message (regardless of whether enhanced or not) is sent 410 to a recipient. The recipient is typically a user of another mobile communication device or other computing device. However, the recipient can also be the another mobile communication device or other computing device. Following the operation 410, the send processing 400 is complete and ends.

Figure 5:
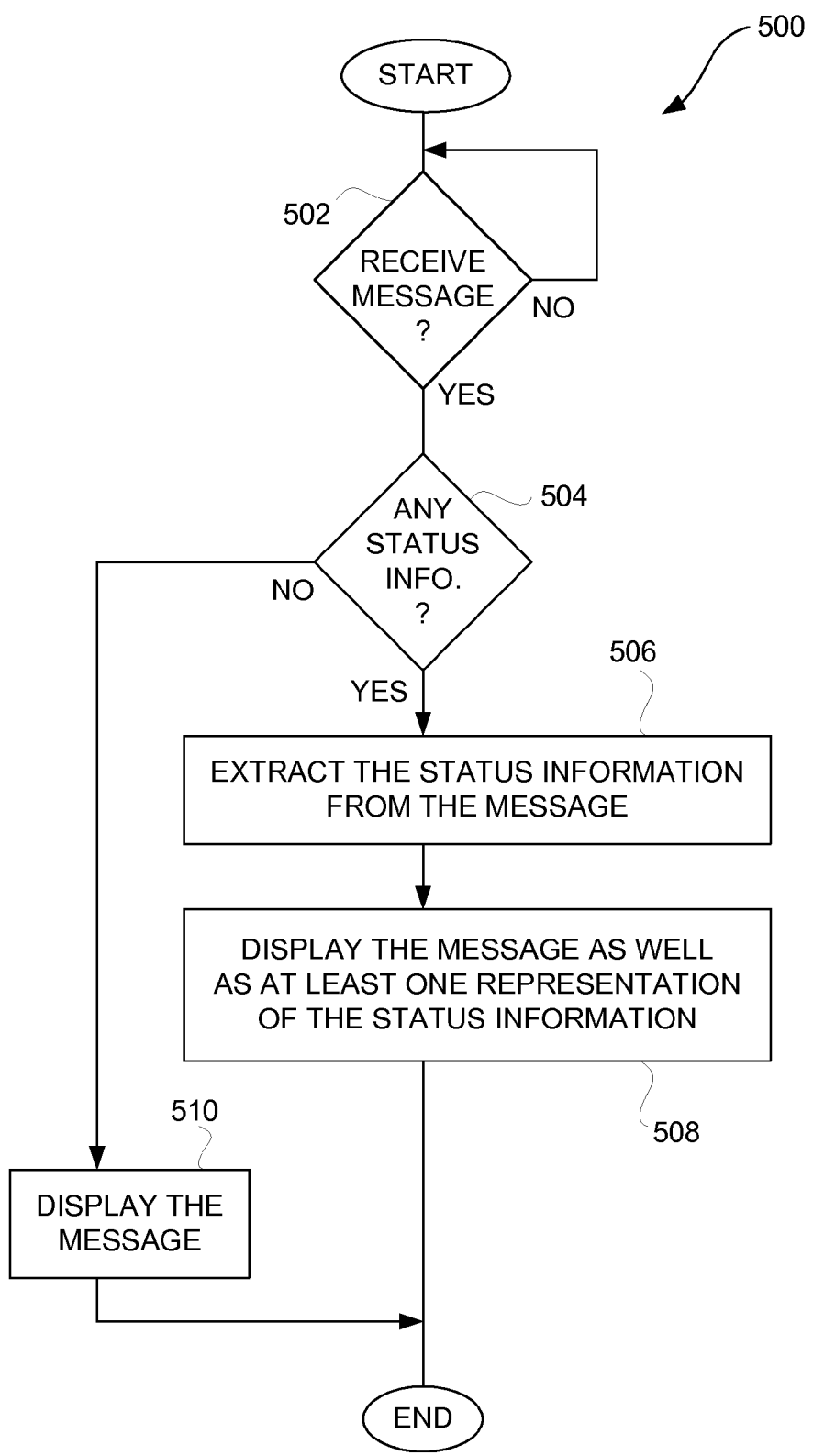
FIG. 5 is a flow diagram of display processing according to one embodiment of the invention.

FIG. 5 is a flow diagram of display processing 500 according to one embodiment of the invention. The display processing 500 is, for example, performed by a mobile communication device or other computing device. The display processing 500 is, for example, performed in response to a message being received due to the send processing 400 of FIG. 4. In other words, the display processing 500 can be performed by a computing device associated with a recipient that has received a message.

The display processing 500 begins with a decision 502 that determines whether a message has been received. When the decision 502 determines that a message has not yet been received, then the display processing 500 awaits the receipt of a message. On the other hand, when the decision 502 determines that a message has been received, a decision 504 then determines whether any status information is provided with the message that has been received. Here, the message is examined to determine whether status information is provided within the message. When the decision 504 determines that status information is provided with the message (and thus the message is an enhanced message), then the status information is extracted 506 from the message.

Next, the message as well as at least one representation of the status information are displayed 508. The representation (e.g., indication) of the status information being displayed can vary with implementation. In one embodiment, the representation is a graphical symbol that represents at least a portion of the status information. For example, a smiling face icon can represent a happy mood, a frown face icon can represent that the user is unhappy, etc. In another embodiment, the representation is textual information that is or represents a portion of the status information. In still another embodiment, the representation is a link (e.g., hyperlink) that provides access to at least a portion of the status information. For such representations, the status information can specify its presentation, or additional processing of the status information can determine an appropriate presentation.

The status information can also be interpreted, analyzed or processed before or while the representation to be displayed is determined. In one embodiment, such interpretation, analysis or processing can be performed, at least in part, by the device sending the message. As one example, the status information can include (or interpreted to include) temperature (e.g., ambient temperature) and user perspiration. Based on these two pieces of status information, one interpretation is that the user is perspiring (i.e., sweating) because of the high temperature.

As another example of the interpretation of status information, relative position of two computing devices can be computed and displayed. For example, if a receiving-computing device (either mobile or stationary) receives position information from a sending-computing device (preferably mobile), then the receiving-computing device (which knows its position) can determine and display the relative position (e.g., distance and/or direction) of the sending and the receiving-computing devices. Further, through use of other conditions information pertaining to the sending-computing device that might also be provided to the receiving-computing device, the receiving-computing device can also display the speed (velocity), direction of travel, etc. of the sending-computing device. Through additional interpretation or analysis of the conditions information, the speed (or average speed) could be used to categorize the type of movement of the sending-computing device, which would be available for display, as a symbol or other indication. As examples, the categories could be auto, bicycle, run, fast walk, slow walk, and stationary.

In yet another example, conditions information can include the user's mood. This can be measured in a number of different ways. One method is discussed in U.S. Pat. No. 5,774,591, entitled, "APPARATUS AND METHOD FOR RECOGNIZING FACIAL EXPRESSIONS AND FACIAL GESTURES IN A SEQUENCE OF IMAGES," which is hereby incorporated herein by reference. Such conditions information can be interpreted at the sending-computing device or the receiving-computing device. Conditions information can be a user's stress level. This piece of status information can, for example, be interpreted and transformed into a symbol, such as a stressed-face icon which the stress level is high. In one embodiment, both the raw data and the symbol(s) are transmitted to a receiving-computing device, but with only the symbol being displayed and the raw data being hidden. By selecting the displayed symbol or through other appropriate user-input, the receiving-computing device can additionally analyze or view the raw data.

Alternatively, when the decision 504 determines that status information is not provided with the message, then the message is displayed 510. Here, there is no status information available to present; therefore, the message is simply displayed. Following the operations 508 and 510, the display processing 500 is complete and ends.

The display processing 500 operates to present at least an indicator or representation of the status information through a display. In another embodiment, the status can be presented to the user of the mobile communication device or other computing device in other ways. For example, the status information could be presented by an audio output (e.g., synthesized voice), a tactile output or other types of outputs that can be sensed by the user, which is typically a living being, such as a human being.

In one aspect of the invention, status information can be automatically included with user-entered messages being sent as noted above. As another aspect of the invention, status information can be acquired and presented on request.

Figure 6:
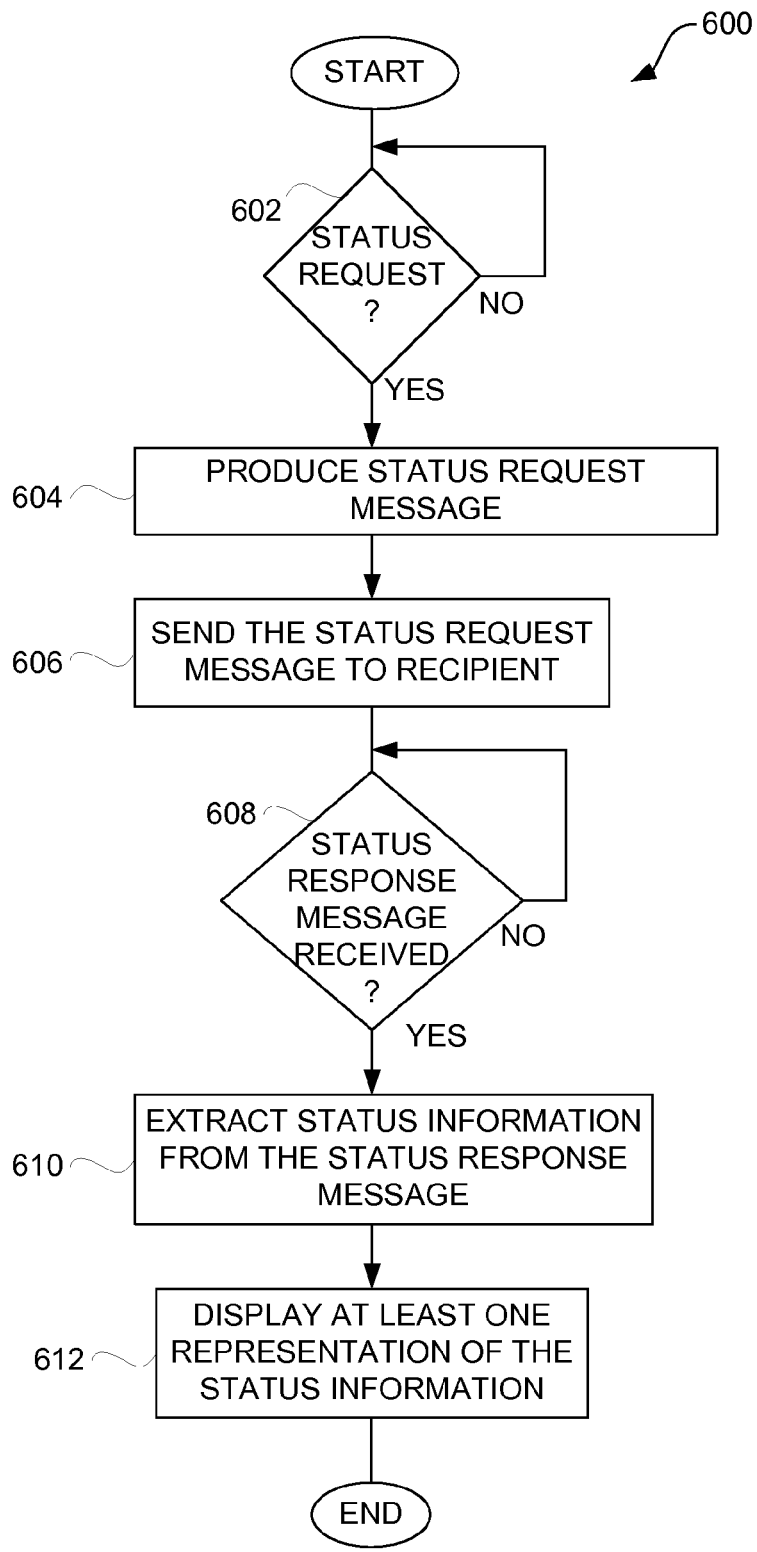
FIG. 6 is a flow diagram of status retrieval processing according to one embodiment of the invention.

FIG. 6 is a flow diagram of status retrieval processing 600 according to one embodiment of the invention. The status retrieval processing 600 is, for example, performed by a mobile communication device or other computing device.

The status retrieval processing 600 begins with a decision 602 that determines whether a status request has been requested. The status request is provided by a requestor to acquire status information from another mobile communication device or other computing device. In one embodiment, the status request is initiated by a requestor. The requestor can be a user of the mobile communication device or other computing device. In another embodiment, the status request can be initiated by the mobile communication device or other computing device. When the decision 602 determines that a status request has not been requested, then the status retrieval processing 600 awaits such a request.

Once the decision 602 determines that a status request has been requested, a status request message is produced 604. The status request message is then sent 606 from the requestor to a recipient. In one embodiment, the status request message is a short text message (e.g., SMS message) that need not be displayed at the recipient. A status request message that is not displayed at the recipient can be referred to as a dummy message. The recipient can be another mobile communication device or other computing device, or a user thereof.

Next, a decision 608 determines whether a status response message has been received by the requestor. The status response message includes status information associated with the recipient. The status response message is a message sent by the recipient in response to the status request message from the requestor. When the decision 608 determines that the status response message has not yet been received, then the status retrieval processing 600 awaits receipt of a status response message. On the other hand, when the decision 608 determines that a status response message (responsive to the status request message) has been received, then the status retrieval processing 600 continues. Namely, status information is extracted 610 from the status response message. Next, at least one representation of the status information is displayed 612. The representation can vary with implementation. In one embodiment, the representation is a graphical symbol that represents at least a portion of the status information. In another embodiment, the representation is text that is or represents a portion of the status information. In another embodiment, the representation is a piece of video clip that is or represents a portion of the status information. In still another embodiment, the representation is a link (e.g., hyperlink) that provides access to at least a portion of the status information. The status information can also be interpreted, analyzed or processed before or while the representation to be displayed is determined. Following the operation 600, the status retrieval processing 600 is complete and ends.

Figure 7:
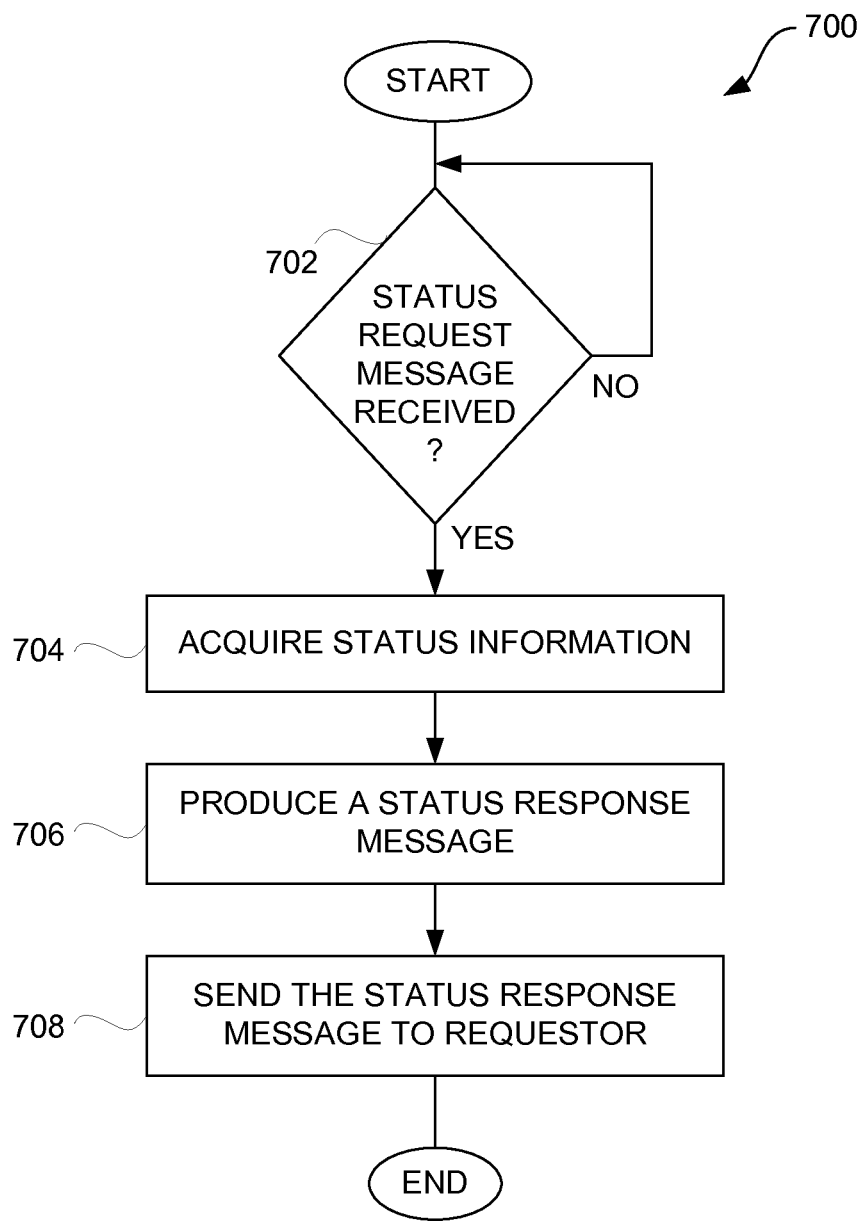
FIG. 7 is a flow diagram of status request processing according to one embodiment of the invention.

FIG. 7 is a flow diagram of status request processing 700 according to one embodiment of the invention. The status request processing 700 is, for example, performed by a mobile communication device or other computing device. The status request processing 700 is, for example, performed in response to a status request message of the status retrieval processing 600 of FIG. 6.

The status request processing 700 begins with a decision 702 that determines whether a status request message has been received. When the decision 702 determines that a status request message has not yet been received, then the status request processing 700 awaits such a message. Once the decision 702 determines that a status request message has been received, status information for the associated mobile communication device or other computing device or user thereof is acquired 704. A status response message is then produced 706 based on the status information. The status response message is then sent 708 to the requestor. The requestor can be considered to be a mobile communication device or other computing device, or a user thereof, that caused the status request message to be sent. According to one embodiment, once the status response message is sent 708, the operations 610-612 of the status retrieval processing 600 of FIG. 6 can be performed.

As described above, status information is typically presented in some manner at the recipient (often presented concurrently with a message). In other embodiments, the status information can be stored in a database for later utilization. The messages can be subsequently searched, sorted or otherwise processed.

In still another aspect of the invention, status information can be automatically sent to one or more recipients whenever available or when changed. For example, one such embodiment could have a mobile communication device periodically or on events (e.g., status events) send its status information to another computing device. As another example, status information could be automatically sent to another computing device when changed by more that a threshold amount. This would enable the another computing device to maintain awareness of up-to-date status information of the mobile communication device. Like other embodiments, this embodiment can operate in a peer-to-peer manner or in a centralized manner.

Note that status sensors do not have to be embedded in a mobile communication device. A status sensor can be physically detached, but electronically coupled to a communication device through a wireless link, such as based on the Bluetooth or Wi-Fi technologies. In yet another embodiment, a status sensor electronically couples to a communication device through a wire connection.

In yet another embodiment, the sending of status information can be through user-activation. In other words, although a piece of status information is acquired via a status sensor, its transmission to another electronic device can depend on a user's voluntary action, such as pushing a button.

One application of the invention is to provide the status information with messages, such as text messages and in particular near real-time text messages, such as instant messages. Hence, users of computing devices, namely, mobile communication devices, can exchange near real-time text messages and in doing so can also exchange status information. In some embodiments, the exchange of status information is achieved automatically, without user initiation.

The messages can be provided in a markup language format. The status information can be embedded or included in the messages also in a markup language. As examples, the markup language include HTML, HDML, WML, XML, etc. The messages and/or status information can also be provided in a programming language format, such as JAVA or C.

Another application of the invention is in the medical area. For example, a patient carries a mobile communication device with a position detector. He is also carrying one or more status sensors that can sense, for example, his body temperature, blood pressure, blood sugar or glucose level, blood oxygen, spirometry, ECG, heart rate, arrhythmias, brain wave, other sound wave measurable by a stethoscope, and/or body fat. The sensors can be non-invasive or invasive. Also, the sensor(s) can be coupled to the device is a wireless or wired manner. Such status information can be transmitted upon his command. In one embodiment, a patient's mobile communication device sends a message ("Very tired.") to an emergency clinic. It is an enhanced message that includes some of the patient's status information, such as his physical location and blood sugar level. In response, a specialist at the clinic sends one or more messages back, instructing the patient how to care for himself and/or controlling the release of insulin into the patient. In the mean time, the specialist can dispatch an ambulance to pick him up.

A number of embodiments have been described based on text messages. The present invention is also applicable to other types of messages, such as voice messages. In one embodiment, the message is provided with a voice call, and the mobile communication device is a mobile telephone (e.g., cell phone).

Also, a number of embodiments have been described regarding a device sending information to another device. In one embodiment, a device can broadcast enhanced messages to many devices.

In yet another embodiment, communication among devices can be monitored and charged by a third party. For example, the user of a communicating device can be billed depending on the amount of enhanced messages he has been sending or the amount or degree of enhancement to messages. In one embodiment, both the recipient and the sender of the enhanced messages are billed. In another embodiment, the more types of status messages included, the higher the bill.

For example, enhanced messages with position, temperature and humidity information will cost more than enhanced messages with just position.

The various aspects can be used separately or in any combination.

The above-described system, methods and processes can be used together with other aspects of a monitoring system or mobile device, including the various aspects described in: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION SYSTEM, METHOD AND APPARATUS FOR ACQUIRING, PRESENTING, MANAGING AND USING POSITION INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

The invention can be implemented in software, hardware or a combination of hardware and software. The invention can also be embodied as computer readable code on a computer readable medium. The computer readable medium can be any data storage device that can store data which can thereafter be read by a computing device. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield one or more of the following advantages. One advantage is that status information is able to be obtained easily while exchanging electronic messages or otherwise through use of electronic messages. Another advantage of the invention is that messages are able to be enhanced with status information acquired by sensors. Still another advantage of the invention is that it can operate in a point-to-point or centralized manner to gather and present status information between computing devices (e.g., mobile communication devices).

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A method to facilitate communication among users of mobile electronic devices, said method comprising:

receiving message content for a text message via the first mobile electronic device;

acquiring status information of the first mobile electronic device, the status information including at least position information regarding position of the first mobile electronic device;

determining a plurality of other mobile electronic devices or users thereof that are authorized to receive the status information;

determining whether at least one user selection has been received via the first mobile electronic device to indicate if the status information is to be provided with the text message, and initiating sending of the text message along with the status information to each of the plurality of other mobile electronic devices via a wireless network, provided that the status information is to be provided with the text message and provided that the plurality of other mobile electronic devices or users thereof are authorized to receive the status information.

2. A method as recited in claim 1, wherein the at least one user selection comprises a user setting at the first mobile electronic device.

3. A method as recited in claim 1, wherein the at least one user selection is received at the first mobile electronic device via a graphical user interface.

4. A method as recited in claim 3, wherein the graphical user interface comprises a dialog box that is displayed at the first mobile electronic device.

5. A method as recited in claim 3, wherein the graphical user interface allows a user to direct that at least a portion of the status information is to be provided with the text message.

6. A method as recited in claim 3, wherein the graphical user interface allows a user to direct that at least a portion of the status information is not to be provided with the text message.

7. A method as recited in claim 3, wherein the graphical user interface allows a user to direct that at least a portion of status information is to be provided with all text messages to be sent by the user of the first mobile electronic device.

8. A method as recited in claim 1, wherein the status information for inclusion with the text message can be set at different levels.

9. A method as recited in claim 1, wherein the method comprises:

modifying the status information acquired from the first mobile electronic device prior to the initiating sending of the text message along with the status information to the plurality of other mobile electronic devices.

10. A method as recited in claim 9, wherein the modifying the status information produces modified status information that includes at least one presentation instruction.

11. A method as recited in claim 10, wherein the at least one presentation instruction is provided at least in part in a markup language.

12. A method as recited in claim 1, wherein the method comprises:

receiving a text message from another mobile electronic device via a wireless network;

determining whether the received text message includes at least status information;

extracting the status information from the received text message when it is determined that the text message includes at least the status information; and displaying at least a portion of the received text message and at least one representation of the status information on a display when it is determined that the received text message includes at least the status information.

13. A method as recited in claim 1, wherein the method comprises:
augmenting the status information acquired from the first mobile electronic device prior to sending such to the plurality of other mobile electronic devices.

14. A method as recited in claim 1, wherein the method comprises:
modifying the position information acquired from the first mobile electronic device.

15. A method as recited in claim 14, wherein the modifying the position information produces modified position information based at least in part on a local network.

16. A method as recited in claim 15, wherein the local network comprises a Wi-Fi network.

17. A method as recited in claim 1, wherein the acquiring the status information is configured to determine the position information based on location data supplied by a GPS receiver provided in the first mobile electronic device.

18. A method as recited in claim 1, wherein the acquiring the status information is configured to determine the position information based on (i) location data supplied by a GPS receiver provided in the first mobile electronic device, and (ii) other location data associated with a local network available for use by the first mobile electronic device.

19. A method as recited in claim 1, wherein the acquiring the status information is configured to receive the position information from a GPS receiver provided in the first mobile electronic device.

20. A method as recited in claim 19,
wherein the method comprises modifying the position information acquired from the first mobile electronic device, and
wherein the modifying the position information is configured to modify the position information from the GPS receiver.

21. A method as recited in claim 1, wherein the initiating sending of the text message along with the status information to each of the plurality of other mobile electronic devices does so in accordance with at least one direction being provided via the first mobile electronic device.

22. A method to facilitate communication among users of mobile electronic devices, said method comprising:
receiving message content for a text message via the first mobile electronic device;
acquiring status information of the first mobile electronic device, the status information including at least position information regarding position of the first mobile electronic device;
determining a plurality of other mobile electronic devices or users thereof that are authorized to receive at least the status information;
determining whether at least one selection has been received from the first mobile electronic device to influence whether the status information is to be provided with the text message;
determining, based at least in part on the at least one selection, whether the status information is to be provided with the text message, provided that the at least one selection has been received; and
initiating sending of the text message along with the status information to each of the plurality of other mobile electronic devices via at least one wireless network, provided that the status information is to be provided with the text message and provided that the plurality of other mobile electronic devices or users thereof are authorized to receive at least the status information.

23. A method as recited in claim 22, wherein the at least one selection is received at the first mobile electronic device via a graphical user interface.

24. A method as recited in claim 23, wherein the graphical user interface allows a user to direct that at least a portion of the status information is not to be provided with the text message.

25. A method as recited in claim 23, wherein the graphical user interface allows a user to generally direct that at least a portion of the status information is to be provided with all text messages to be sent by the user of the first mobile electronic device.

26. A method as recited in claim 22, wherein the status information for inclusion with a text message can be set at different levels.

27. A method as recited in claim 22, wherein the method comprises:
modifying the status information acquired from the first mobile electronic device prior to the initiating sending of the text message along with the status information to the plurality of other mobile electronic devices.

28. A method as recited in claim 22, wherein the method comprises:
receiving a text message from another mobile electronic device via a wireless network;
determining whether the received text message includes at least status information;
extracting the status information from the received text message when it is determined that the received text message includes at least the status information; and
displaying at least a portion of the received text message and at least onE representation of the status information when it is determined that the received text message includes at least the status information.

29. A method as recited in claim 22, wherein the acquiring the status information is configured to determine the position information based on (i) location data supplied by a GPS receiver provided in the first mobile electronic device, and (ii) other location data associated with a local network available for use by the first mobile electronic device.

30. A method as recited in claim 22,
wherein the acquiring the status information comprises:
receiving the position information; and
modifying the position information received from the first mobile electronic device to provide modified position information, and
wherein the initiating sending of the text message along with the status information to each of the plurality of other mobile electronic devices comprises the initiating sending of the text message along with the modified position information to each of the plurality of other mobile electronic devices.

31. A method as recited in claim 30, wherein the receiving of the position information comprises receiving the position information from a GPS receiver provided in the first mobile electronic device.

32. A method as recited in claim 22, wherein the initiating sending of the text message along with the status information to each of the plurality of other mobile electronic devices does so in accordance with at least one direction received from the first mobile electronic device.

33. A method to facilitate communication among users of mobile electronic devices, said method comprising:
receiving message content for a text message via the first mobile electronic device;

acquiring position information of the first mobile electronic device;

determining a plurality of other mobile electronic devices or users thereof that are authorized to receive the position information;

determining whether at least one indication has been received from the first mobile electronic device to indicate if the position information is to be provided with the text message, and initiating sending of the text message along with the position information to each of the plurality of other mobile electronic devices via at least one wireless network, provided that the position information is to be provided with the text message and provided that the plurality of other mobile electronic devices or users thereof are authorized to receive the position information.

34. A method as recited in claim 33, wherein the method comprises:

modifying the position information acquired from the first mobile electronic device, and wherein the position information used by the inviting sending is the modified position information.

35. A method as recited in claim 34, wherein the modifying the position information produces modified position information based at least in part on a local network.

36. A method as recited in claim 35, wherein the local network comprises a Wi-Fi network.

37. A method as recited in claim 33, wherein the acquiring the position information comprises:

receiving location data supplied by a GPS receiver provided in the first mobile electronic device; and determining the position information based on the location data supplied by the GPS receiver provided in the first mobile electronic device.

38. A method as recited in claim 33, wherein the acquiring the position information comprises:

receiving location data supplied by a GPS receiver provided in the first mobile electronic device; and determining the position information based on (i) the location data supplied by the GPS receiver provided in the first mobile electronic device, and (ii) other location data associated with a local network available for use by the first mobile electronic device.

39. A method as recited in claim 33, wherein the acquiring the status information is configured to receive the position information provided at least in part by a GPS receiver provided in the first mobile electronic device.

40. A method as recited in claim 39, wherein the method comprises modifying the position information acquired from the first mobile electronic device, and wherein the position information used by the inviting sending is the modified position information.

* * * * *

UNITED STATES PATENT AND TRADEMARK OFFICE
CERTIFICATE OF CORRECTION

PATENT NO.        : 8,447,822 B2                                           Page 1 of 1
APPLICATION NO.   : 13/459025
DATED             : May 21, 2013
INVENTOR(S)       : Lau et al.

It is certified that error appears in the above-identified patent and that said Letters Patent is hereby corrected as shown below:

On Title Page 4, under Other Publications:
In right column, line 70, "www.axiomnay" should be --www.axiomnav--.

On Title Page 5, under Other Publications:
In the left column, line 47, "The Star-Ledger Ledger" should be --The Star-Ledger--.

In the Claims:
Column 16, line 34 (claim 28, line 11) "at least onE" should be --at least one--.

Signed and Sealed this
Third Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,447,822 B2 | Page 1 of 1 |
| APPLICATION NO. | : 13/459025 | |
| DATED | : May 21, 2013 | |
| INVENTOR(S) | : Lau et al. | |

It is certified that error appears in the above-identified patent and that said Letters Patent is hereby corrected as shown below:

In the Claims:

In column 17, line 21, "inviting" should be --initiating--.

In column 18, line 25, "inviting" should be --initiating--.

Signed and Sealed this
Twenty-eighth Day of July, 2015

Michelle K. Lee
*Director of the United States Patent and Trademark Office*